(12) United States Patent
Kodama et al.

(10) Patent No.: US 11,193,068 B2
(45) Date of Patent: Dec. 7, 2021

(54) COMPOUND, LIQUID CRYSTAL COMPOSITION, CURED SUBSTANCE, OPTICAL ANISOTROPIC BODY, AND REFLECTION FILM

(71) Applicant: FUJIFILM Corporation, Tokyo (JP)

(72) Inventors: Keisuke Kodama, Kanagawa (JP); Shunya Katoh, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 58 days.

(21) Appl. No.: 16/655,236

(22) Filed: Oct. 17, 2019

(65) Prior Publication Data
US 2020/0071615 A1    Mar. 5, 2020

Related U.S. Application Data

(63) Continuation of application No. PCT/JP2018/016288, filed on Apr. 20, 2018.

(30) Foreign Application Priority Data

Apr. 20, 2017 (JP) .............................. JP2017-083458
Apr. 13, 2018 (JP) .............................. JP2018-077675

(51) Int. Cl.
C09K 19/58 (2006.01)
C09K 19/32 (2006.01)
(Continued)

(52) U.S. Cl.
CPC .......... C09K 19/586 (2013.01); C09K 19/322 (2013.01); C09K 19/3444 (2013.01);
(Continued)

(58) Field of Classification Search
CPC .... C09K 19/58; C09K 19/582; C09K 19/586; C09K 19/588; C09K 2019/323
See application file for complete search history.

(56) References Cited

U.S. PATENT DOCUMENTS

2004/0142116 A1   7/2004  Nishikawa et al.
2007/0122565 A1*  5/2007  Shundo ................. C09K 19/32
                                              428/1.1
(Continued)

FOREIGN PATENT DOCUMENTS

JP    2004231641    8/2004
JP    2007176927    7/2007
(Continued)

OTHER PUBLICATIONS

"International Search Report (Form PCT/ISA/210) of PCT/JP2018/016288", dated Jun. 5, 2018, with English translation thereof, pp. 1-5.
(Continued)

*Primary Examiner* — Chanceity N Robinson
*Assistant Examiner* — Anna Malloy
(74) *Attorney, Agent, or Firm* — JCIPRNET

(57) ABSTRACT

A compound has a strong HTP and a high temperature dependence of HTP. In addition, a liquid crystal composition, a cured substance, an optical anisotropic boy, and a reflection film the above-described compound. The compound is represented by General Formula (1), wherein $X^1$ and $X^2$ each independently represent —CH=CH— or C≡C—.
(Continued)

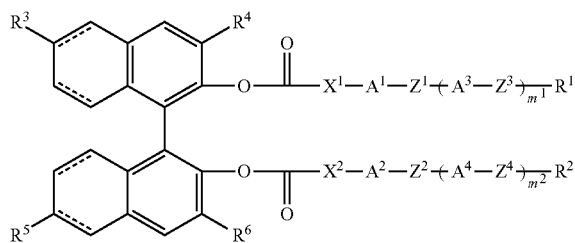

(1)

18 Claims, 1 Drawing Sheet

(51) Int. Cl.
    *C09K 19/34*     (2006.01)
    *G02F 1/1333*    (2006.01)
    *G02F 1/1335*    (2006.01)
    *C09K 19/04*     (2006.01)

(52) U.S. Cl.
    CPC .... *C09K 19/3483* (2013.01); *G02F 1/133305* (2013.01); *G02F 1/133553* (2013.01); *C09K 2019/0448* (2013.01); *C09K 2019/323* (2013.01)

(56) References Cited

U.S. PATENT DOCUMENTS

2014/0342086 A1   11/2014   Ibn-Elhaj et al.
2016/0011349 A1*  1/2016   Hirai .................... C09K 19/04
                                      349/193

FOREIGN PATENT DOCUMENTS

| JP | 2013087109 | 5/2013 |
| JP | 2014097938 | 5/2014 |
| JP | 2014532104 | 12/2014 |

OTHER PUBLICATIONS

"Written Opinion of the International Searching Authority (Form PCT/ISA/237) of PCT/JP2018/016288", dated Jun. 5, 2018, with English translation thereof, pp. 1-8.

* cited by examiner

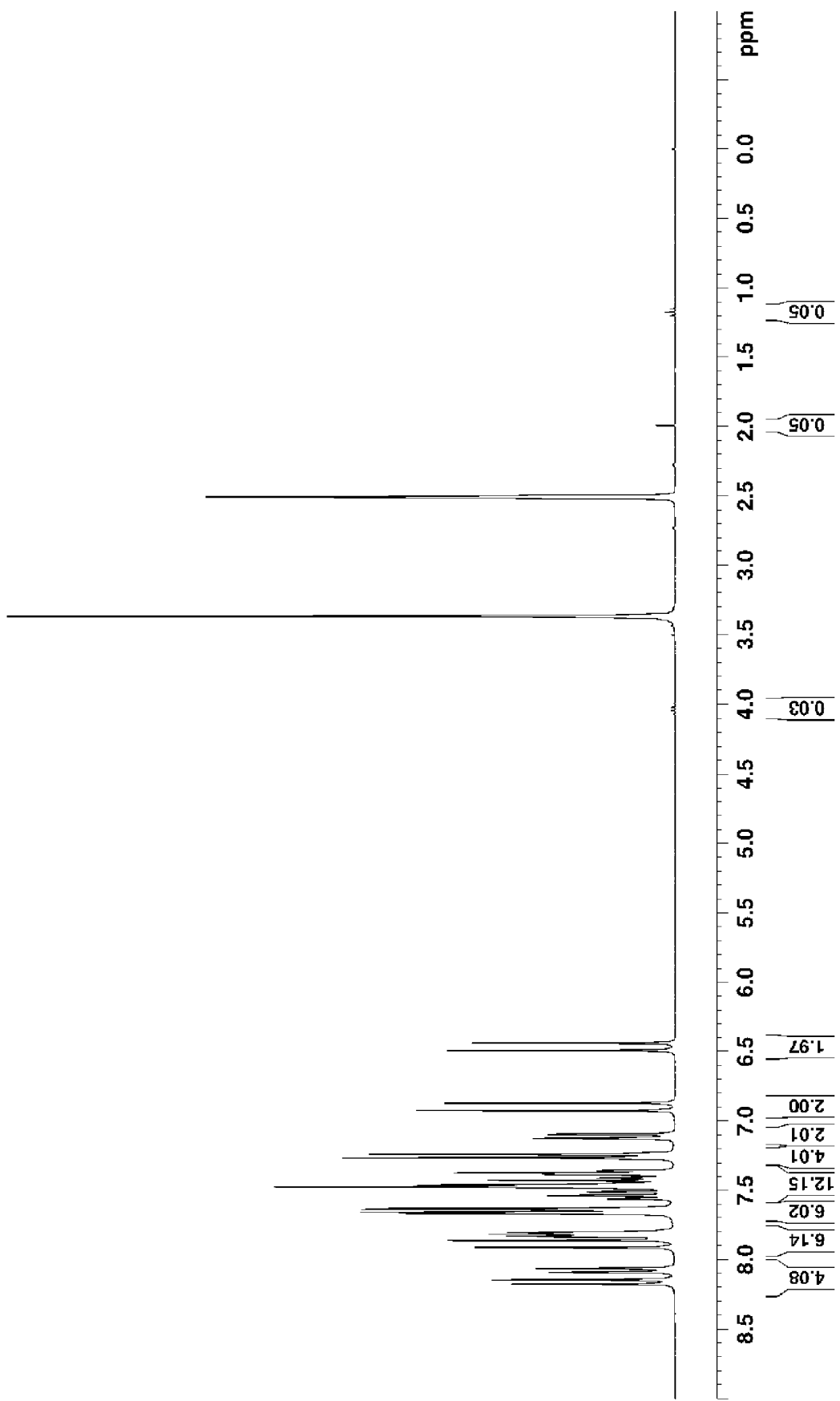

COMPOUND, LIQUID CRYSTAL COMPOSITION, CURED SUBSTANCE, OPTICAL ANISOTROPIC BODY, AND REFLECTION FILM

CROSS-REFERENCE TO RELATED APPLICATIONS

This application is a Continuation of PCT International Application No. PCT/JP2018/016288 filed on Apr. 20, 2018, which claims priority under 35 U.S.C. § 119(a) to Japanese Patent Application No. 2017-083458 filed on Apr. 20, 2017 and Japanese Patent Application No. 2018-077675 filed on Apr. 13, 2018. Each of the above applications is hereby expressly incorporated by reference, in its entirety, into the present application.

BACKGROUND OF THE INVENTION

1. Field of the Invention

The present invention relates to a compound, a liquid crystal composition, a cured substance, an optical anisotropic body, and a reflection film.

2. Description of the Related Art

A compound exhibiting liquid crystallinity (hereinafter, also referred to as "liquid crystalline compound") can be applied to a variety of applications. For example, the liquid crystalline compound is applied to the manufacturing of an optical anisotropic body represented by a phase difference film or the manufacturing of a reflection film formed by fixing a cholesteric liquid crystal phase.

Generally, the cholesteric liquid crystal phase is formed by adding a chiral compound to a nematic liquid crystal. In JP2007-176927A and JP2013-087109A, as a polymerizable chiral compound having a strong helical twisting power (HTP), polymerizable chiral compounds having a binaphthyl skeleton are disclosed.

SUMMARY OF THE INVENTION

Recently, a chiral compound having a strong HTP and significantly changing the intensity of HTP depending on temperature (in other words, a chiral compound having HTP with a strong temperature dependence) has been desired.

The present inventors studied the chiral compound described in JP2007-176927A and found that there is a need for improving HTP (increasing HTP). In addition, the present inventors studied the chiral compound described in JP2013-087109A and found that there is a need for improving the temperature dependence of HTP.

Therefore, an object of the present invention is to provide a compound having a strong HTP and a high temperature dependence of HTP.

In addition, another object of the present invention is to provide a liquid crystal composition, a cured substance, an optical anisotropic boy, and a reflection film in which the above-described compound is used.

The present inventors carried out intensive studies in order to achieve the above-described objects, consequently found that the above-described objects can be achieved using a compound represented by General Formula (1) below, and completed the present invention.

That is, it was found that the above-described objects can be achieved by the following configurations.

[1] A compound represented by General Formula (1) below.

[2] The compound according to [1], in which the $A^1$ and the $A^2$ each are independently a five- or more-membered aromatic hydrocarbon ring group which may have a substituent.

[3] The compound according to [1] or [2], in which the $A^1$ and the $A^2$ each are independently a phenylene group which may have a substituent.

[4] The compound according to any one of [1] to [3], in which the $X^1$ and the $X^2$ are —CH=CH—.

[5] The compound according to any one of [1] to [4], in which the $A^3$ and the $A^4$ each are independently a five- or more-membered aromatic hydrocarbon ring group which may have a substituent.

[6] The compound according to any one of [1] to [5], in which the $Z^1$ and the $Z^2$ each are independently —COO—, —OCO—, —CH=CH—COO—, —CH=CH—OCO—, —COO—CH=CH—, or —OCO—CH=CH—.

[7] The compound according to any one of [1] to [6], in which the $Z^1$ and the $Z^2$ each are independently —CH=CH—COO—, —CH=CH—OCO—, —COO—CH=CH—, or —OCO—CH=CH—.

[8] The compound according to any one of [1] to [7], in which the $Z^3$ and the $Z^4$ each are independently a single bond, —CH=CH—COO—, —CH=CH—OCO—, —COO—CH=CH—, or —OCO—CH=CH—.

[9] A liquid crystal composition comprising: a liquid crystalline compound; and the compound according to any one of [1] to [8].

[10] The liquid crystal composition according to [9], in which the liquid crystalline compound is a liquid crystalline compound having at least one polymerizable group.

[11] The liquid crystal composition according to [10], in which the liquid crystalline compound is a compound represented by General Formula (2) below.

[12] A cured substance formed using the liquid crystal composition according to any one of [9] to [11].

[13] An optical anisotropic body formed using the liquid crystal composition according to any one of [9] to [11].

[14] A reflection film formed using the liquid crystal composition according to any one of [9] to [11].

According to the present invention, it is possible to provide a compound having a strong HTP and a high temperature dependence of HTP.

In addition, according to the present invention, it is possible to provide a liquid crystal composition, a cured substance, an optical anisotropic boy, and a reflection film in which the above-described compound is used.

BRIEF DESCRIPTION OF THE DRAWING

FIG. 1 is a $^1$HNMR (nuclear magnetic resonance) spectrum of a compound CD-1 that is a compound represented by General Formula (1).

DESCRIPTION OF THE PREFERRED EMBODIMENTS

Hereinafter, the present invention will be described in detail.

Configurational requirements mentioned below will be described on the basis of typical embodiments of the present invention, but the present invention is not limited to such embodiments.

In the present specification, numerical ranges expressed using "to" include numerical values described before and after "to" as the lower limit value and the upper limit value.

In addition, in the present specification, "a (meth)acryloyloxy group" refer to both an acryloyloxy group and a methacryloyloxy group.

[Compound Represented by General Formula (1)]

As characteristic points of a compound represented by General Formula (1) of the present invention, the compound has a partial structure represented by General Formula (1A) and has specific organic groups at bonding positions of *$^a$ and *$^b$ respectively.

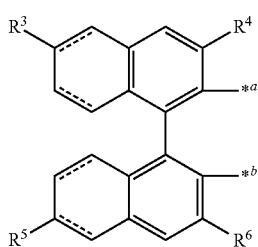

(1A)

In General Formula (1A), a portion in which a solid line and a broken line are parallel to each other indicates a single bond or a double bond. That is, General Formula (1A) is represented by General Formula (1A-1) in a case where the portion in which a solid line and a broken line are parallel to each other indicates a single bond and is represented by General Formula (1A-2) in a case where the portion in which a solid line and a broken line are parallel to each other indicates a double bond.

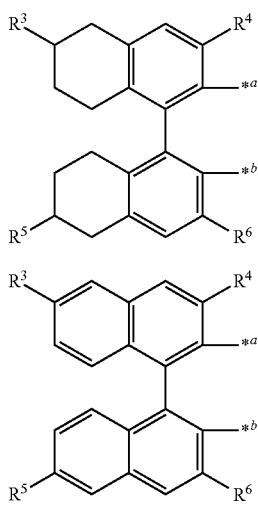

(1A-1)

(1A-2)

Particularly, the compound represented by General Formula (1) of the present invention has characteristics in that (1) the respective specific organic groups bonding to *$^a$ and *$^b$ bond to the *$^a$ and *$^b$ sites through a —OCO—X$^1$-A$^1$- group (or a —OCO—X$^2$-A$^2$- group) in the specific organic groups and (2) the respective specific organic groups have two or more five- or more-membered hydrocarbon ring groups or heterocyclic groups (A$^1$ and A$^3$, and A$^2$ and A$^4$).

The compound represented by General Formula (1) of the present invention is assumed to have a high temperature dependence of HTP since the above-described configuration (1) facilitates the movement of the partial structure represented by General Formula (1A) and has a strong HTP due to the above-described configuration (2).

Hereinafter, the compound represented by General Formula (1) (chiral compound) will be described in detail below.

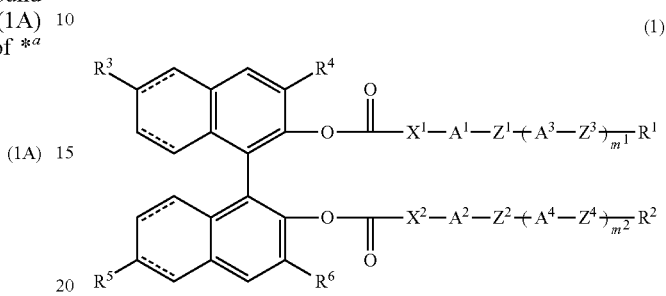

(1)

In General Formula (1), $X^1$ and $X^2$ each independently represent —CH=CH— or —C≡C—. $A^1$ to $A^4$ each independently represent a five- or more-membered hydrocarbon ring group or a five- or more-membered heterocyclic group which may have a substituent. $Z^1$ to $Z^4$ each independently represent a single bond or a divalent linking group. $m^1$ and $m^2$ each independently represent an integer of 1 to 5. $R^1$ to $R^6$ each independently represent a hydrogen atom or a monovalent substituent. The portion in which a solid line and a broken line are parallel to each other represents a single bond or a double bond.

In General Formula (1), $X^1$ and $X^2$ each independently represent —CH=CH— or —C≡C—. $X^1$ and $X^2$ are preferably —CH=CH— since the temperature dependence of HTP becomes higher.

In General Formula (1), $A^1$ to $A^4$ each independently represent a five- or more-membered hydrocarbon ring group or a five- or more-membered heterocyclic group which may have a substituent. In addition, in a case where there is a plurality of $A^3$'s, $A^3$'s may be identical to or different from each other. This is also true for $A^4$.

As the hydrocarbon ring group represented by $A^1$ to $A^4$, a five- or more-membered aliphatic hydrocarbon ring group and a five- or more-membered aromatic hydrocarbon ring group are exemplified. The upper limit of the number of ring members is not particularly limited, but is often 10 or less.

An aliphatic hydrocarbon ring that configures the aliphatic hydrocarbon ring group may be any of a monocyclic structure or a polycyclic structure. In a case where the aliphatic hydrocarbon ring is a polycyclic structure, at least one ring included in the polycyclic structure needs to be a five- or more-membered ring.

The number of carbon atoms in the aliphatic hydrocarbon ring is not particularly limited, but is preferably 5 to 12, more preferably 5 to 10, and still more preferably 5 or 6. As specific examples of the aliphatic hydrocarbon ring, cyclopentane, cyclohexane, cycloheptane, cyclooctane, norbornene, adamantine, and the like are exemplified. Among them, cyclohexane is preferred. In the case of removing two hydrogen atoms on the ring, the aliphatic hydrocarbon ring configures the aliphatic hydrocarbon ring group.

An aromatic hydrocarbon ring configuring the aromatic hydrocarbon ring group may be any of a monocyclic structure or a polycyclic structure. In a case where the aromatic hydrocarbon ring is a polycyclic structure, at least one ring included in the polycyclic structure needs to be a five- or more-membered ring.

The number of carbon atoms in the aromatic hydrocarbon ring is not particularly limited, but is preferably 6 to 18 and more preferably 6 to 10. As specific examples of the aromatic hydrocarbon ring, a benzene ring, a biphenyl ring, a naphthalene ring, an anthracene ring, a phenanthrene ring, and a fluorene ring are exemplified. Among them, a benzene ring is preferred. In the case of removing two hydrogen atoms on the ring, the aromatic hydrocarbon ring configures the aromatic hydrocarbon ring group.

As the heterocyclic group represented by $A^1$ to $A^4$, a five- or more-membered aliphatic heterocyclic group and a five- or more-membered aromatic heterocyclic group are exemplified. The upper limit of the number of ring members is not particularly limited, but is often 10 or less.

An aliphatic heterocycle that configures the aliphatic heterocyclic group may be any of a monocyclic structure or a polycyclic structure. In a case where the aliphatic heterocycle is a polycyclic structure, at least one ring included in the polycyclic structure needs to be a five- or more-membered ring.

As a hetero atom included in the aliphatic heterocycle, for example, a nitrogen atom, an oxygen atom, and a sulfur atom are exemplified. The number of carbon atoms in the aliphatic heterocycle is not particularly limited, but is preferably 5 to 10. As specific examples of the aliphatic heterocycle, for example, oxolanes, oxanes, piperidines, piperazines, and the like are exemplified. The aliphatic heterocycle may be an aliphatic heterocycle in which —$CH_2$— configuring the ring is substituted with —CO—, and, for example, a phthalimide ring and the like are exemplified.

In the case of removing two hydrogen atoms on the ring, the aliphatic heterocycle configures the aliphatic heterocyclic group.

An aromatic heterocycle configuring the aromatic heterocyclic group may be any of a monocyclic structure or a polycyclic structure. In a case where the aromatic heterocycle is a polycyclic structure, at least one ring included in the polycyclic structure needs to be a five- or more-membered ring.

As a hetero atom included in the aromatic heterocyclic group, for example, a nitrogen atom, an oxygen atom, and a sulfur atom are exemplified. The number of carbon atoms in the aromatic heterocycle is not particularly limited, but is preferably 5 to 18. As specific examples of the aromatic heterocycle, for example, a pyridine ring, a pyridazine ring, a pyrimidine ring, a pyrazine ring, a triazine ring, a thiophene ring, a thiazole ring, and an imidazole ring are exemplified. In the case of removing two hydrogen atoms on the ring, the aromatic heterocycle configures the aromatic heterocyclic group.

As $A^1$ and $A^2$, since the temperature dependence of HTP becomes higher, the five- or more-membered aromatic hydrocarbon ring group which may have a substituent is preferred and a phenylene group which may have a substituent is more preferred.

As $A^3$ and $A^4$, since the temperature dependence of HTP becomes higher, the five- or more-membered aromatic hydrocarbon ring group which may have a substituent is preferred.

$A^1$ to $A^4$ may have a substituent. The substituent is not particularly limited, well-known substituents are exemplified, and, for example, a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group are exemplified. The respective groups described above may be further substituted with a substituent. For example, a hydrogen atom in an alkyl group may be substituted with a fluorine atom.

In General Formula (1), $Z^1$ to $Z^4$ each independently represent a single bond or a divalent linking group.

The divalent linking group is not particularly limited, and, for example, a divalent aliphatic hydrocarbon group (which may be linear, branched, or cyclic and preferably has 1 to 20 carbon atoms; for example, an alkylene group is exemplified. Additionally, the divalent aliphatic hydrocarbon group may be an alkenylene group or an alkynylene group), —O—, —S—, —$SO_2$—, —$NR^1$—, —CO—(—C(=O)—), —COO—(—C(=O)O—), —OCO—(—OC(=O)—), —$NR^1$—CO—, —CO—$NR^1$—, —$SO_3$—, —$SO_2NR^1$—, —$NR^1SO_2$—, —N=N—, —CH=N—, —N=CH—, and groups formed by combining two or more of the above-described groups are exemplified. Here, $R^1$ represents a hydrogen atom or an alkyl group (preferably having 1 to 10 carbon atoms).

A hydrogen atom in the divalent linking group may be substituted with another substituent such as a halogen atom.

As the divalent linking group represented by $Z^1$ to $Z^4$, since the temperature dependence of HTP becomes higher, —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO— —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C— are preferred.

Since the temperature dependence of HTP becomes higher, $Z^1$ and $Z^2$ are preferably —COO—, —OCO—, —CH=CH—COO—, —CH=CH—OCO—, —COO—CH=CH—, or —OCO—CH=CH— and more preferably —CH=CH—COO—, —CH=CH—OCO—, —COO—CH=CH—, or —OCO—CH=CH—.

Since the temperature dependence of HTP becomes higher, $Z^3$ and $Z^4$ are preferably a single bond, —CH=CH—COO—, —CH=CH—OCO—, —COO—CH=CH—, or —OCO—CH=CH—.

In General Formula (1), in a case where there is a plurality of $Z^3$'s, $Z^3$'s may be identical to or different from each other. This is also true for $Z^4$.

In General Formula (1), $m^1$ and $m^2$ each independently represent an integer of 1 to 5.

The number of $m^1$'s and $m^2$'s is not particularly limited, but is preferably an integer of 1 to 3.

In General Formula (1), $R^1$ to $R^6$ each independently represent a hydrogen atom or a monovalent substituent.

The monovalent substituent represented by $R^1$ to $R^6$ is not particularly limited, and well-known substituents are exemplified.

As the monovalent substituent, for example, a halogen atom, an alkyl group, an alkenyl group, an alkynyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group are exemplified. The respective groups described above may be further substituted with a substituent. For example, a hydrogen atom in an alkyl group may be substituted with a fluorine atom.

In addition, the monovalent substituent may be an organic group including a polymerizable group.

The kind of the polymerizable group is not particularly limited, well-known polymerizable groups are exemplified, and, from the viewpoint of reactivity, a functional group capable of an addition polymerization reaction is preferred, and a polymerizable ethylenic unsaturated group or a ring polymerizable group is more preferred. As the polymerizable group, for example, a (meth)acryloyloxy group, a vinyl group, a maleimide group, an acetyl group, a styryl group, an allyl group, an epoxy group, an oxetane group, groups including these groups, and the like are exemplified. A hydrogen atom in the respective groups described below may be substituted with another substituent such as a halogen atom.

As preferred specific examples of the polymerizable group, groups represented by General Formulae (P-1) to (P-20) are exemplified. * in the following formulae represents a bonding position. In addition, Ra represents a hydrogen atom or a methyl group. In addition, Me represents a methyl group, and Et represents an ethyl group.

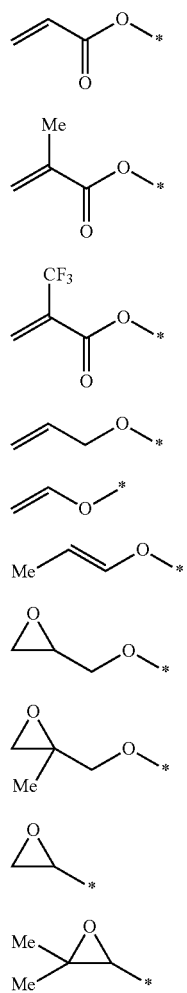

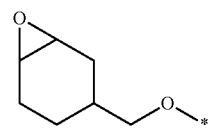

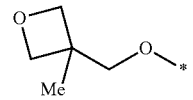

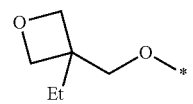

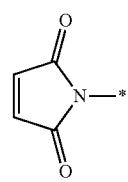

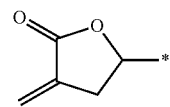

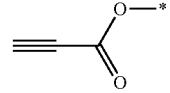

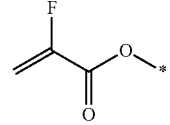

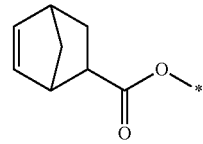

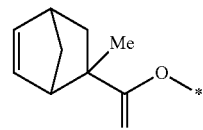

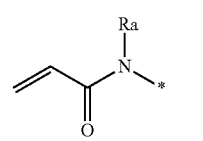

The organic group including the polymerizable group is not particularly limited as long as the organic group contains the above-described polymerizable group.

As the organic group including the polymerizable group, specifically, a group represented by General Formula (PA) is exemplified.

$$*-L^A-P$$    General Formula (PA):

In General Formula (PA), $L^A$ represents a single bond or a divalent linking group. P represents a group represented by General Formulae (P-1) to (P-20). * represents a bonding position (for example, in a case where the monovalent substituent represented by $R^1$ and $R^2$ represents the group represented by General Formula (PA), * represents a bonding position between $Z^3$ ($A^3$ in a case where $Z^3$ is a single bond) and $Z^4$ ($A^4$ in a case where $Z^4$ is a single bond)).

The divalent linking group represented by $L^A$ is not particularly limited, and, for example, a linking group selected from the group consisting of linear or branched alkylene groups having 1 to 20 carbon atoms and linear or branched alkylene groups having 1 to 20 carbon atoms in which one or more —CH$_2$—'s are substituted with —O—, —S—, —NH—, —N(CH$_3$)—, —CO—, —OCO—, or —COO—. As the divalent linking group represented by $L^A$, a group obtaining by substituting one or more —CH$_2$—'s in a linear or branched alkylene groups having 1 to 20 carbon atoms with —O— is preferred, and a group obtaining by substituting one or more —CH$_2$—'s in a linear or branched alkylene groups having 1 to 10 carbon atoms with —O— is more preferred. Particularly, a —O-alkylene group (as the alkylene group, a linear or branched alkylene group having 1 to 6 carbon atoms is preferred, and a linear or branched alkylene group having 1 to 3 carbon atoms is more preferred) is particularly preferred.

In General Formula (1), the portion in which a solid line and a broken line are parallel to each other represents a single bond or a double bond. In a case where the portion in which a solid line and a broken line are parallel to each other indicates a single bond, the compound represented by General Formula (1) corresponds to a compound represented by General Formula (1A-3), and, in a case where the portion in which a solid line and a broken line are parallel to each other indicates a double bond, the compound represented by General Formula (1) corresponds to a compound represented by General Formula (1A-4). The compound represented by General Formula (1) is preferably, particularly, the compound represented by General Formula (1A-4) since the effect of the present invention is superior.

$X^1, X^2, A^1$ to $A^4, Z^1$ to $Z^4, m^1, m^2$, and $R^1$ to $R^6$ in General Formula (1A-3) and General Formula (1A-4) are respectively identical to $X^1, X^2, A^1$ to $A^4, Z^1$ to $Z^4, m^1, m^2$, and $R^1$ to $R^6$ in General Formula (1), and preferred aspects thereof are also identical thereto.

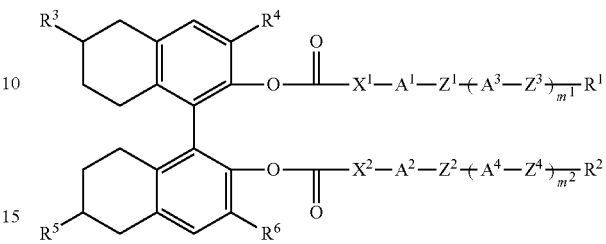

(1A-3)

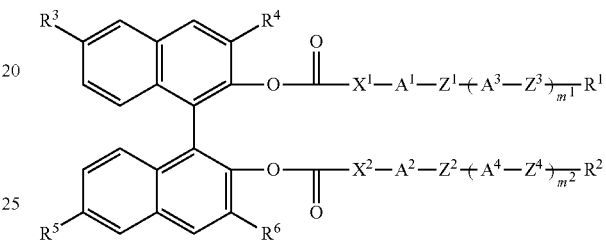

(1A-4)

The compound represented by General Formula (1) can be synthesized using a well-known method.

The compound represented by General Formula (1) may be an R body or an S body or may be a mixture of an R body and an S body.

Hereinafter, specific examples of the compound represented by General Formula (1) will be shown, but are not limited thereto. In the following compounds, there will be cases where only an R body or only an S body is exemplified, but a corresponding S body and a corresponding R body can also be used.

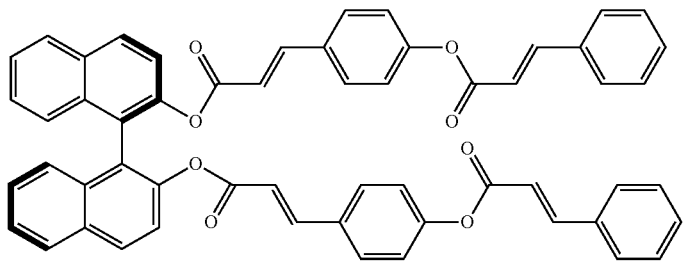

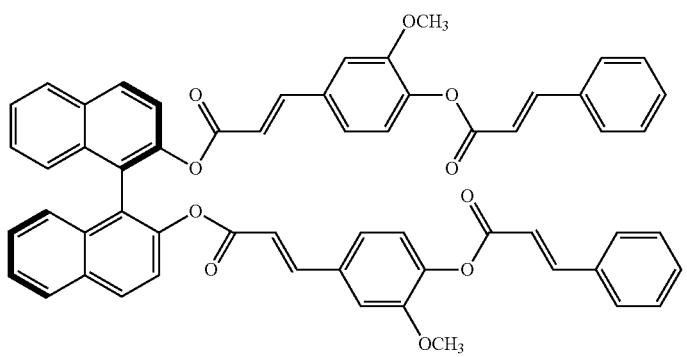

-continued
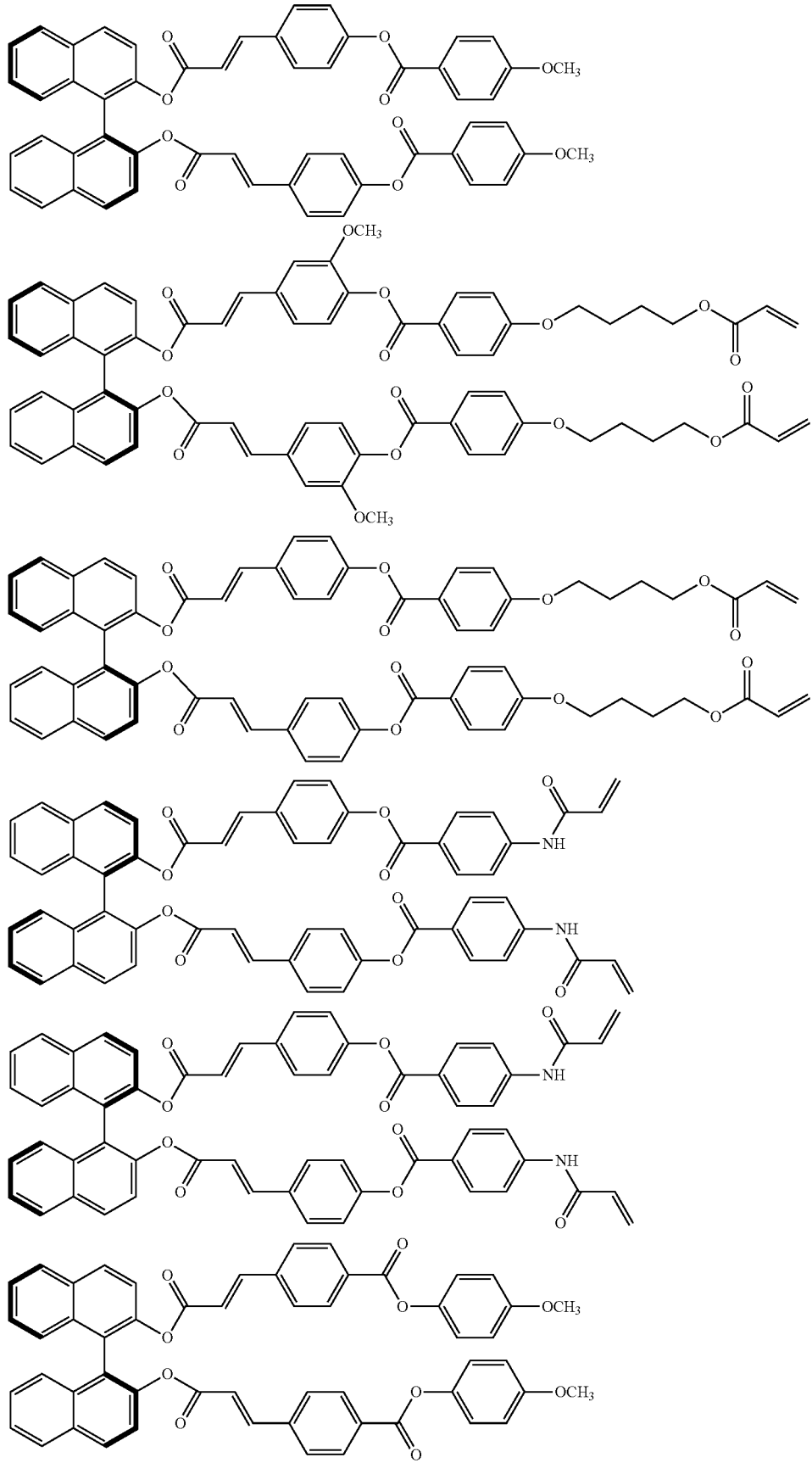

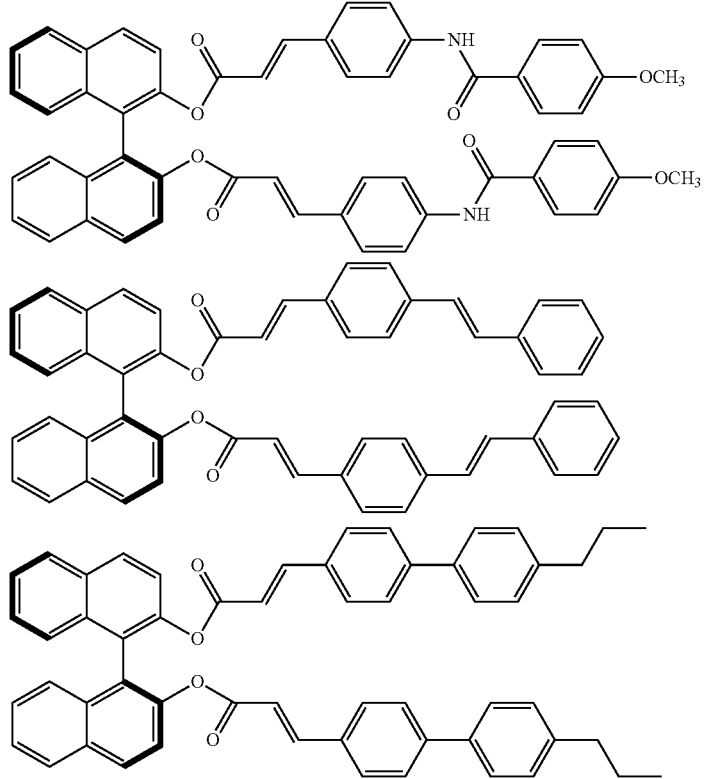
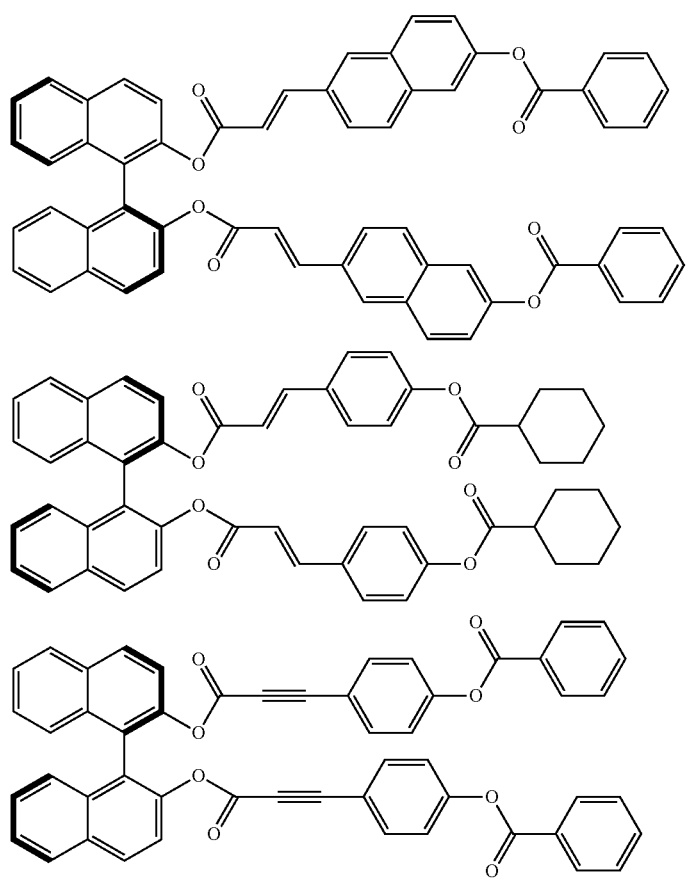

-continued
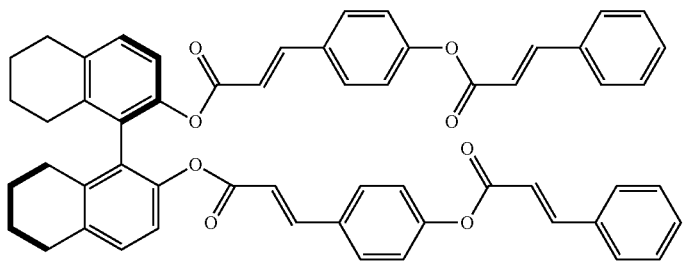
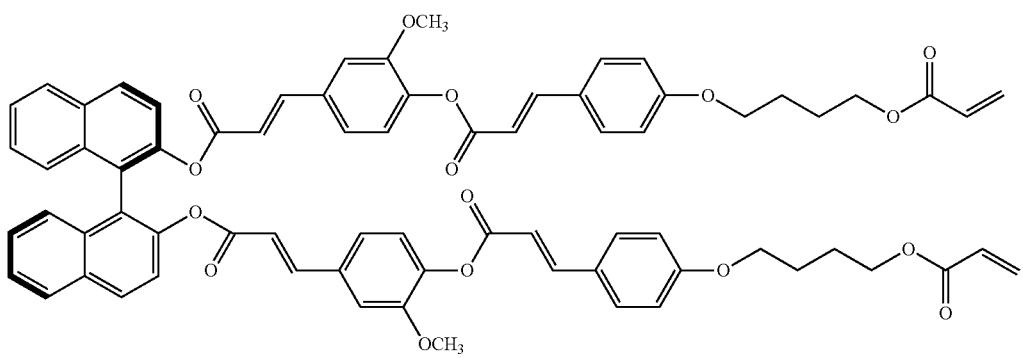
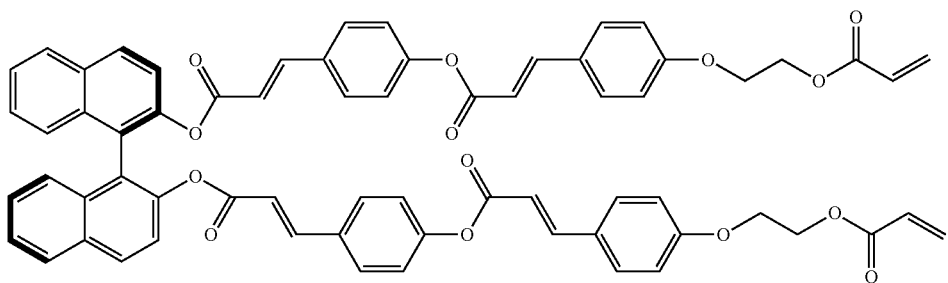
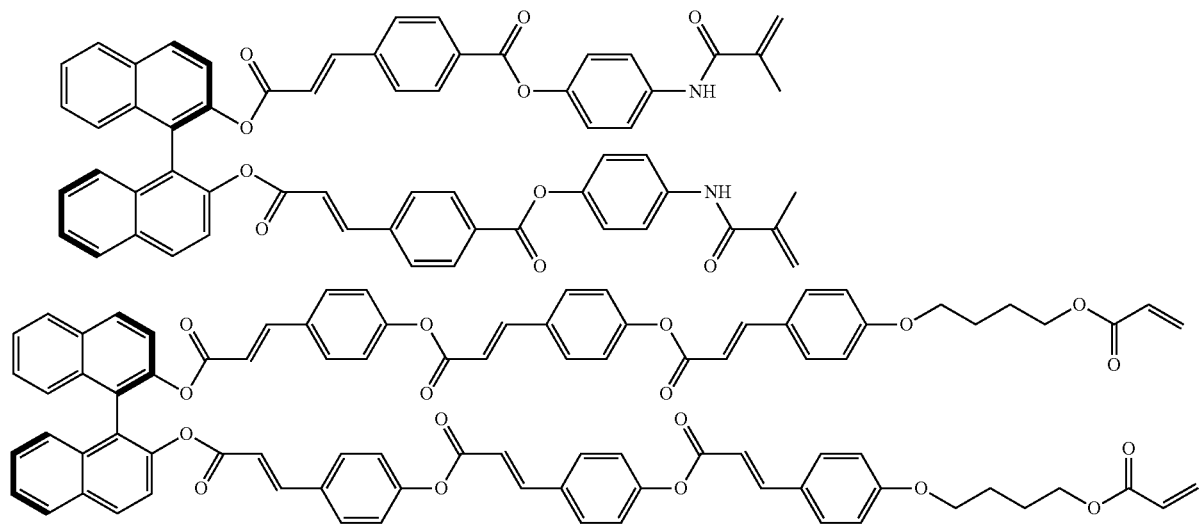

-continued
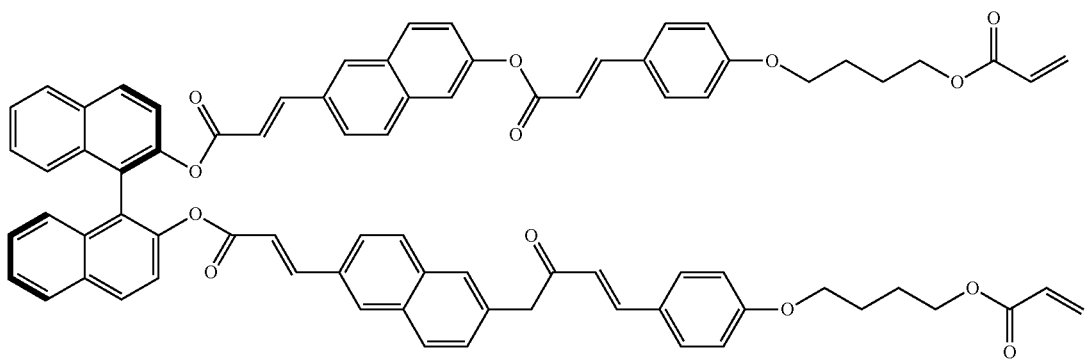
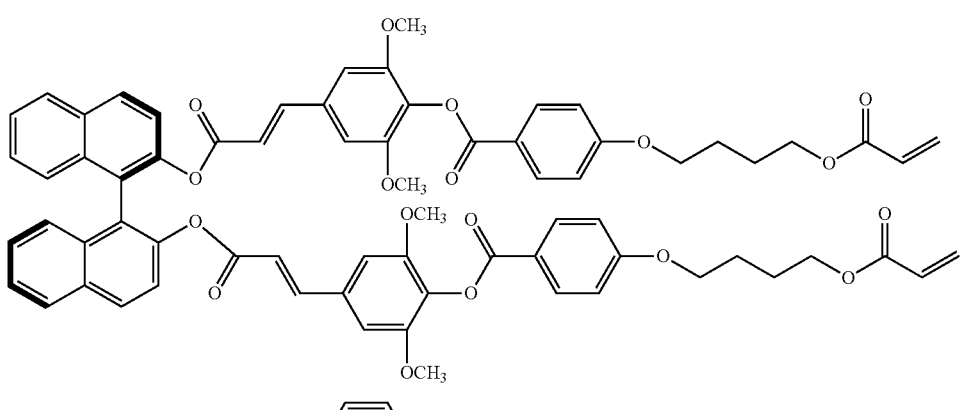
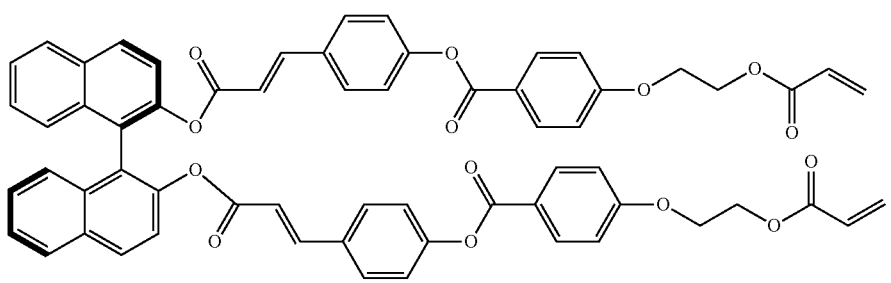
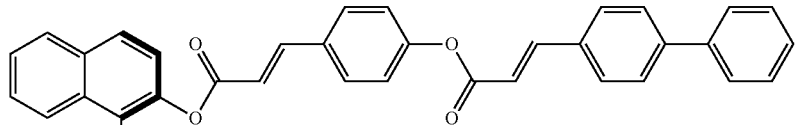
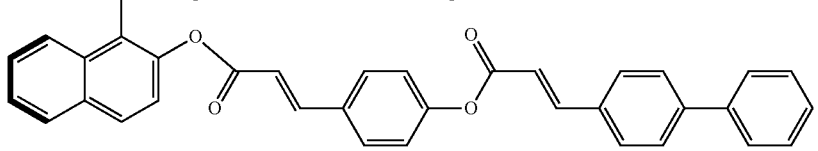
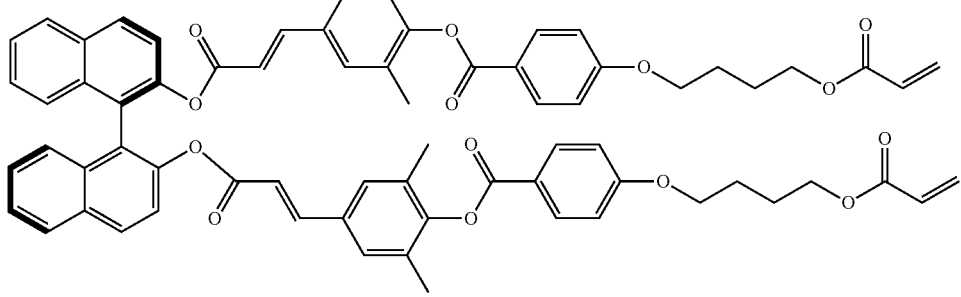

-continued
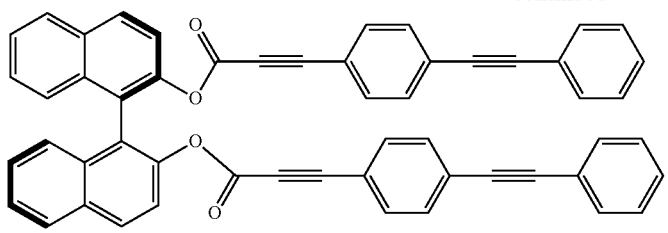
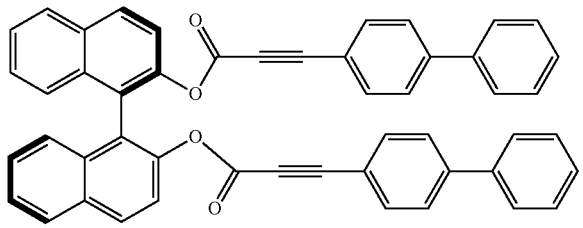
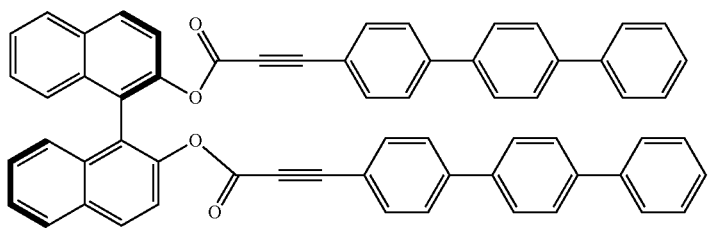
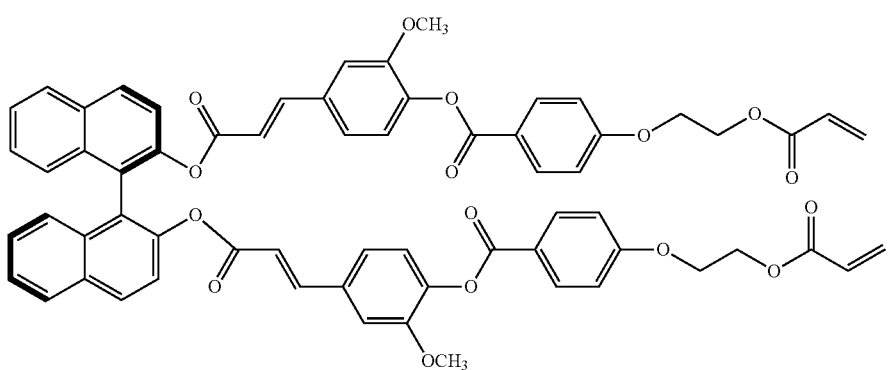
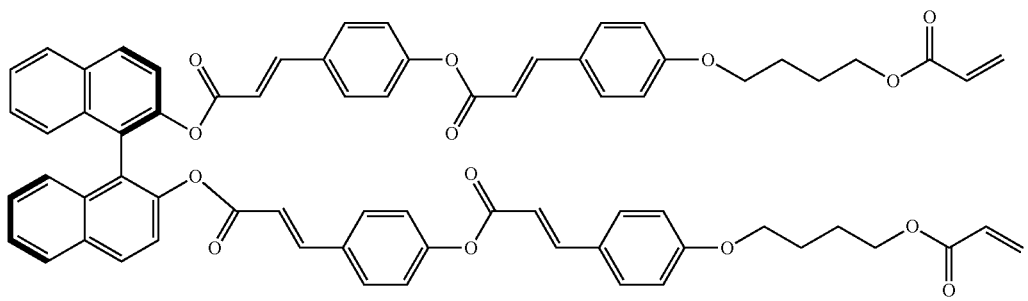

-continued
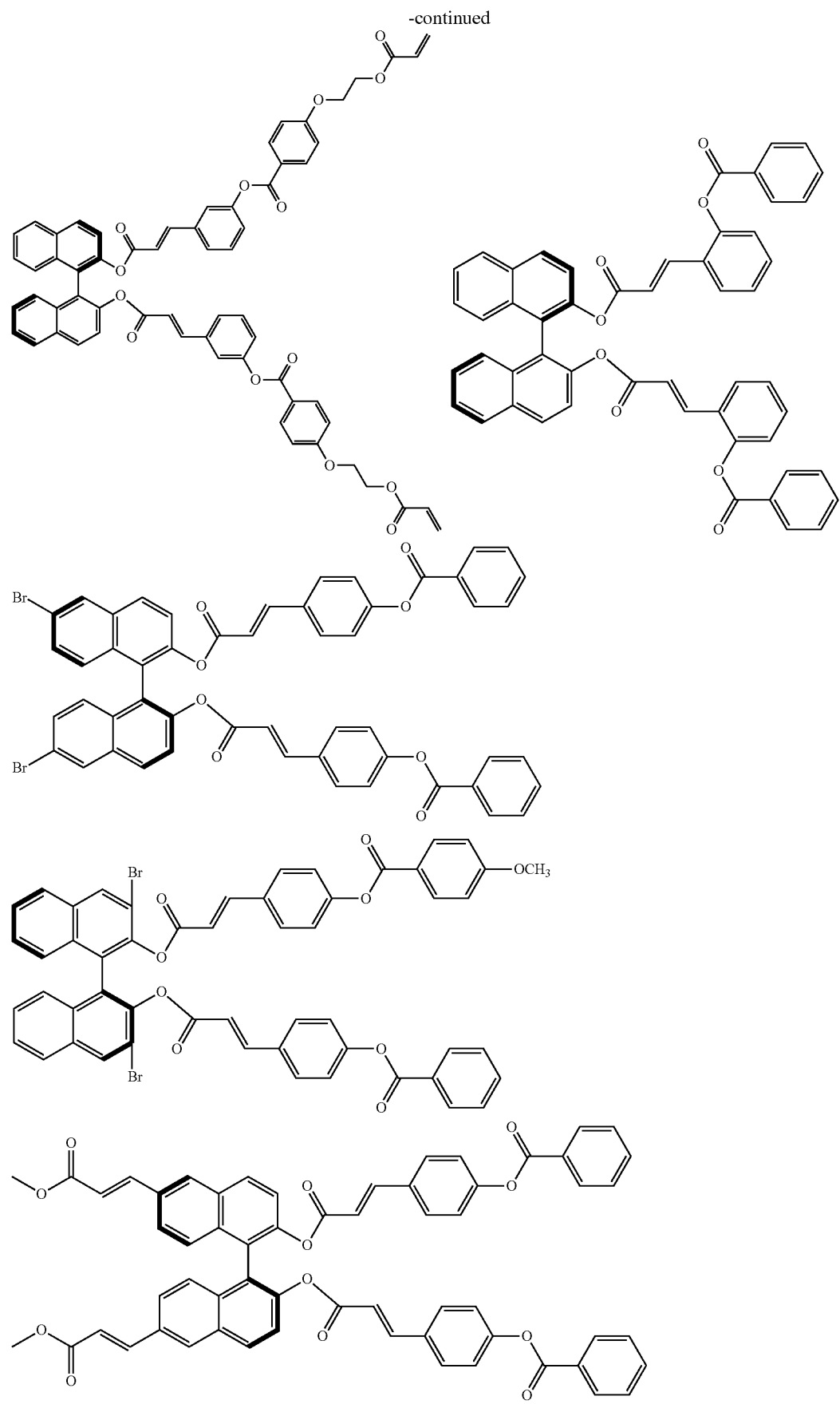

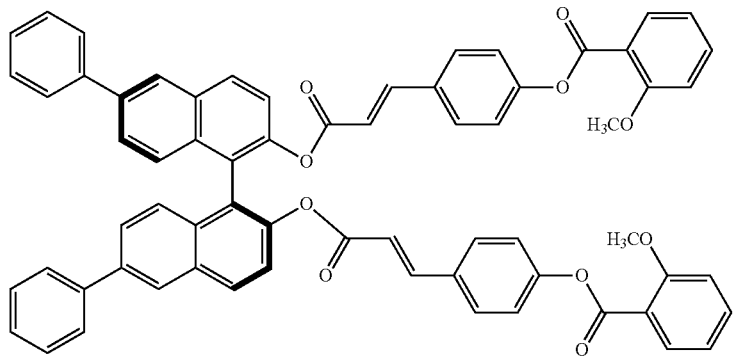
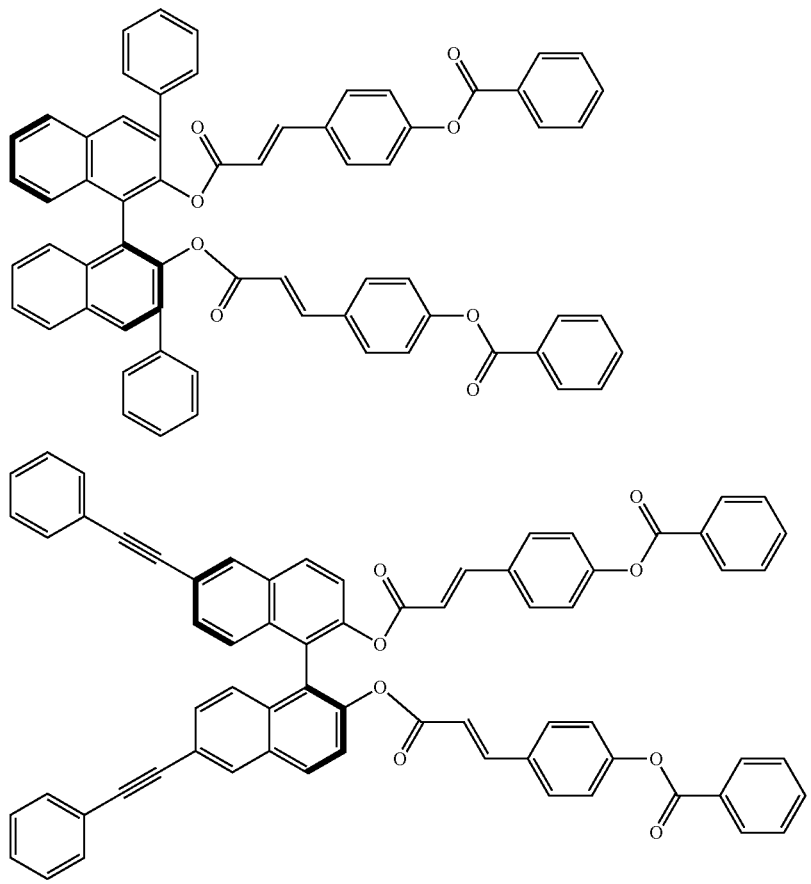
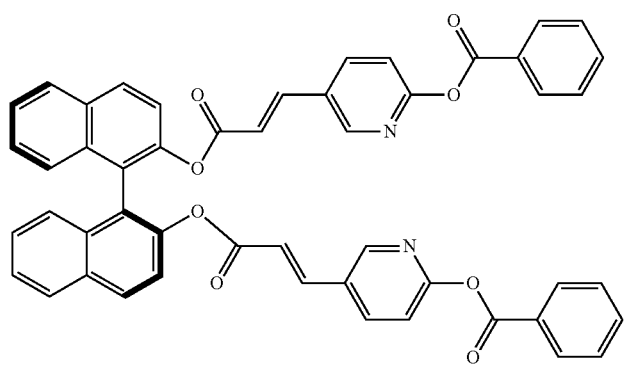

-continued
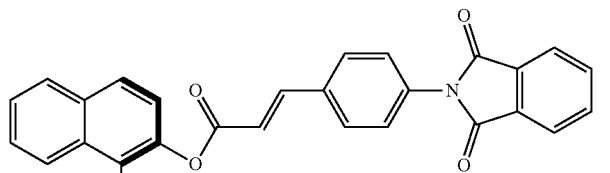
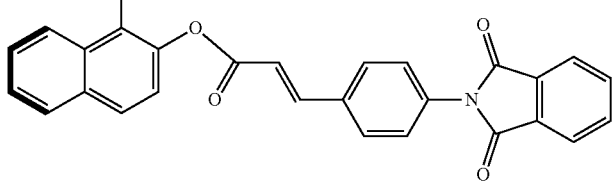
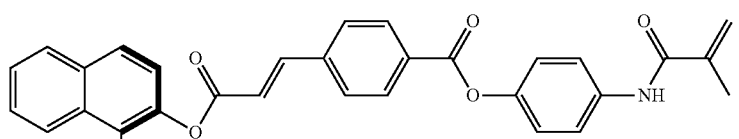
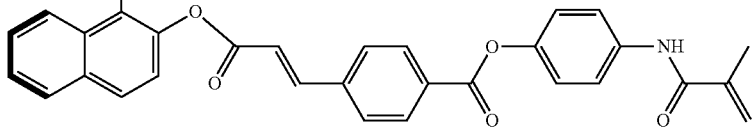
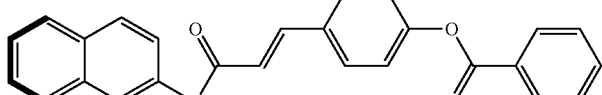
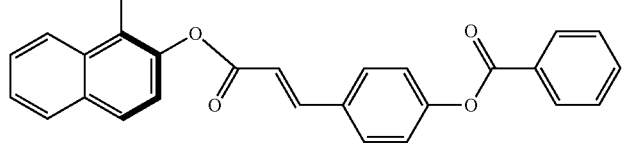
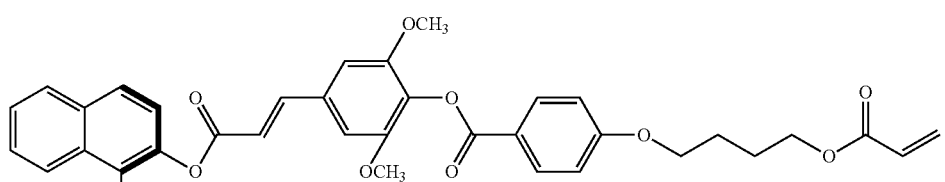
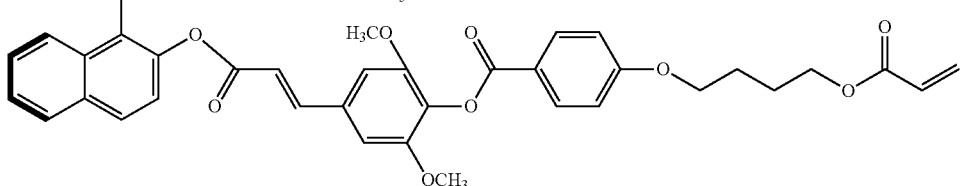
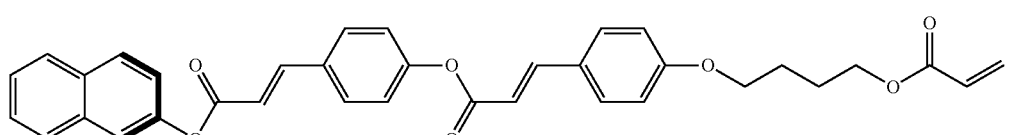
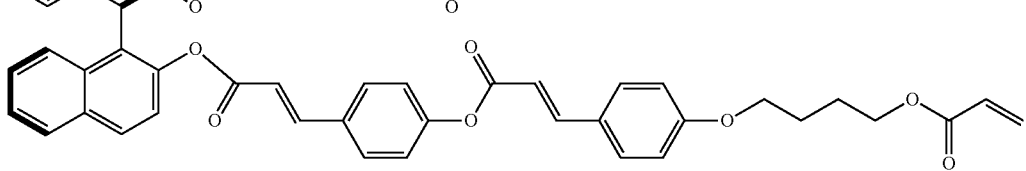

-continued

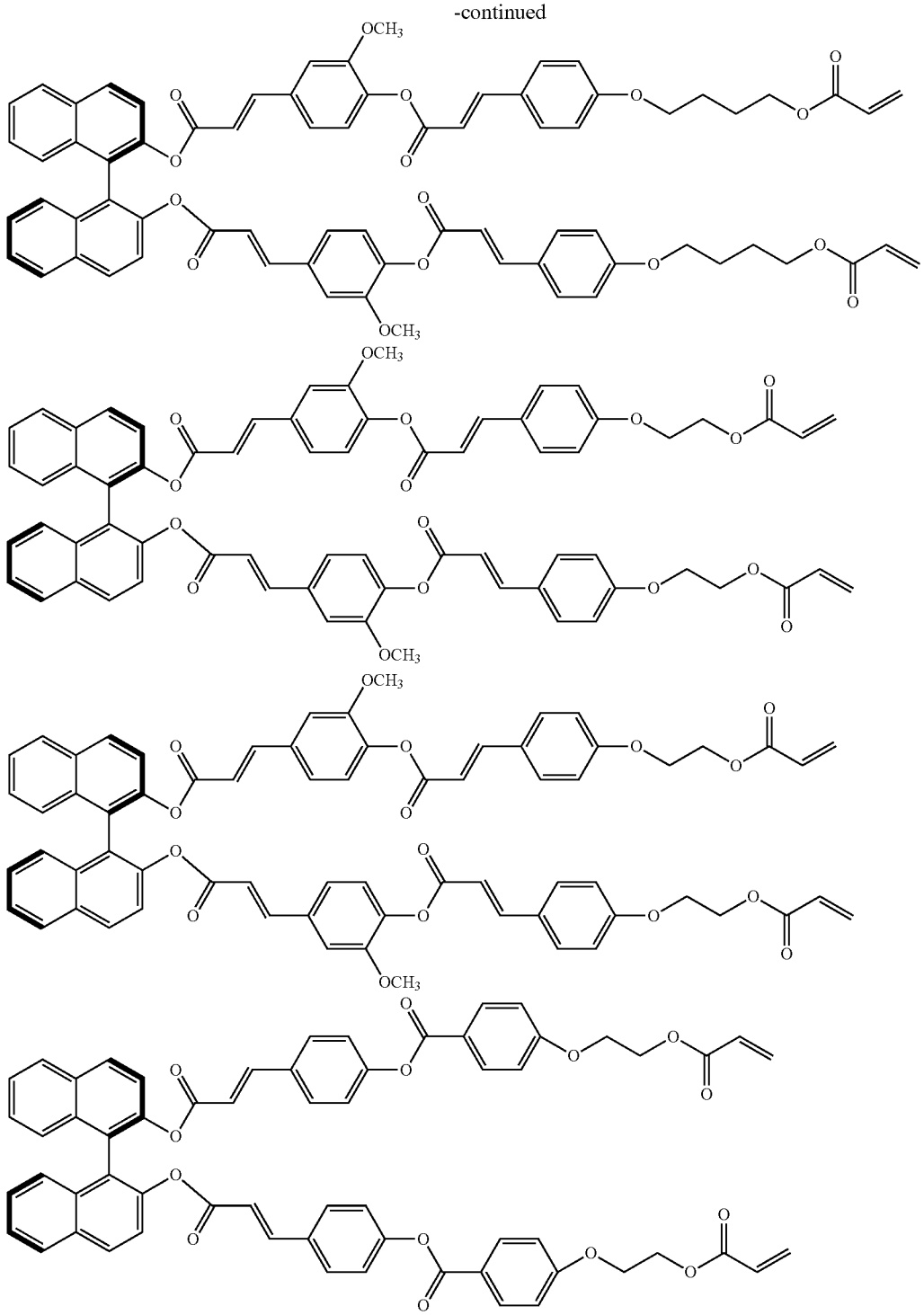

The compound represented by General Formula (1) is a so-called chiral compound and can be applied to a variety of applications. For example, in the case of using a liquid crystal composition obtained by mixing the compound represented by General Formula (1) and a liquid crystalline compound, it is possible to form a cholesteric liquid crystal phase.

Hereinafter, the liquid crystal composition will be described in detail.

[Liquid Crystal Composition]

Next, a liquid crystal composition of an embodiment of the present invention will be described.

The liquid crystal composition of the embodiment of the present invention contains a liquid crystalline compound and the compound represented by General Formula (1).

Hereinafter, the respective components included in the liquid crystal composition of the embodiment of the present invention will be described.

<Liquid Crystalline Compound>

The liquid crystalline compound refers to a compound exhibiting liquid crystallinity. A compound exhibiting liquid crystallinity means that the compound has a property of developing an intermediate phase between a crystal phase (low temperature side) and an isotropic phase (high temperature side) in a case where the temperature is changed. As a specific observation method, optical anisotropy and fluidity derived from a liquid crystal phase can be confirmed by observing the liquid crystalline compound under a polarization microscope while heating or cooling the compound using a hot stage system FP90 manufactured by Mettler Toledo or the like.

The liquid crystalline compound is not particularly limited as long as the compound has liquid crystallinity, and, for example, a rod-shaped nematic liquid crystalline compound and the like are exemplified.

As the rod-shaped nematic liquid crystalline compound, for example, azomethines, azoxys, cyanobiphenyls, cyanophenyl esters, benzoic acid esters, cyclohexanecarboxylic acid phenyl esters, cyanophenylcyclohexanes, cyano substituted phenyl pyrimidines, alkoxy substituted phenyl pyrimidines, phenyl dioxanes, tolanes, alkenyl cyclohexyl benzonitriles, and the like are exemplified. Not only a low-molecular-weight liquid crystalline compound but also a high-molecular-weight liquid crystalline compound can be used.

The liquid crystalline compound may be polymerization or non-polymerizable.

Rod-shaped liquid crystalline compounds having no polymerizable group are described in a variety of documents (for example, Y. Goto et. al., Mol. Cryst. Liq. Cryst. 1995, Vol. 260, pp. 23 to 28).

A polymerizable rod-shaped liquid crystalline compound is obtained by introducing a polymerizable group to a rod-shaped liquid crystalline compound. Examples of the polymerizable group include an unsaturated polymerizable group, an epoxy group, an aziridinyl group, and the like, an unsaturated polymerizable group is preferred, and an ethylenic unsaturated polymerizable group is more preferred. The polymerizable group can be introduced to the molecule of the rod-shaped liquid crystalline compound using a variety of methods. The number of the polymerizable groups in the polymerizable rod-shaped liquid crystalline compound is preferably 1 to 6 and more preferably 1 to 3. Two or more kinds of polymerizable rod-shaped liquid crystalline compound may be jointly used. In a case where two or more kinds of polymerizable rod-shaped liquid crystalline compound are jointly used, it is possible to decrease the orientation temperature.

As the liquid crystalline compound, since the cholesteric liquid crystal phase can be fixed, a liquid crystalline compound having at least one polymerizable group is preferred, and a liquid crystalline compound having at least two polymerizable groups is more preferred.

As the liquid crystalline compound, a compound represented by General Formula (2) is preferred.

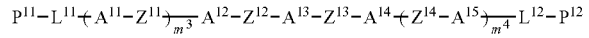

(2)

In General Formula (2), $P^{11}$ and $P^{12}$ each independently represent a hydrogen atom or a polymerizable group. Here, at least one of $P^{11}$ or $P^{12}$ represents a polymerizable group. $L^{11}$ and $L^{12}$ each independently represent a single bond or a divalent linking group. $A^{11}$ to $A^{15}$ each independently represent an aromatic hydrocarbon ring group or an aromatic heterocyclic group which may have a substituent. $Z^{11}$ to $Z^{14}$ each independently represent a single bond or a divalent linking group. $m^3$ and $m^4$ each independently represent an integer of 0 or 1.

In General Formula (2), the polymerizable group represented by $P^{11}$ and $P^{12}$ is not particularly limited, and, for example, the polymerizable groups represented by General Formulae (P-1) to (P-20) are exemplified.

At least one of $P^{11}$ or $P^{12}$ represents a polymerizable group, and both preferably represent a polymerizable group.

In General Formula (2), the divalent linking group represented by $L^{11}$ and $L^{12}$ is not particularly limited, and, for example, a linking group selected from the group consisting of linear or branched alkylene groups having 1 to 20 carbon atoms and linear or branched alkylene groups having 1 to 20 carbon atoms in which one or more —CH$_2$—'s are substituted with —O—, —S—, —NH—, —N(CH$_3$)—, —CO—, —OCO—, or —COO—. As the divalent linking group represented by $L^{11}$ and $L^{12}$, a group obtaining by substituting one or more —CH$_2$—'s in a linear or branched alkylene groups having 1 to 20 carbon atoms with —O— is preferred.

In General Formula (2), $A^{11}$ to $A^{15}$ each independently represent an aromatic hydrocarbon ring group or an aromatic heterocyclic group which may have a substituent.

The definitions of the aromatic hydrocarbon ring group and the aromatic heterocyclic group are identical to the definitions of the aromatic hydrocarbon ring group and the aromatic heterocyclic group described in the above-described paragraph of $A^1$ to $A^4$. The aromatic hydrocarbon ring group and the aromatic heterocyclic group may have a substituent. The kind of the substituent is not particularly limited, and well-known substituents are exemplified. For example, a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitrile group, and an alkoxycarbonyl group are exemplified. The respective groups described above may be further substituted with a substituent. For example, a hydrogen atom in an alkyl group may be substituted with a fluorine atom. In addition, the number of the substituents is not particularly limited, and the aromatic hydrocarbon ring group and the aromatic heterocyclic group may have one substituent or may have a plurality of substituents.

Among them, since the solubility of the compound represented by General Formula (2) further improves, the substituent is preferably a fluorine atom, a chlorine atom, a fluoroalkyl group, an alkoxy group, or an alkyl group and more preferably a fluoroalkyl group, an alkoxy group, or an alkyl group.

The number of carbon atoms in the fluoroalkyl group and the alkyl group and the number of carbon atoms in the alkyl group in the alkoxy group are not particularly limited, but are preferably 1 to 10, more preferably 1 to 5, still more preferably 1 to 3, and particularly preferably 1.

The fluoroalkyl group refers to an alkyl group in which at least one hydrogen atom is substituted with a fluorine atom, and all hydrogen atoms are preferably substituted with fluorine atoms (a so-called perfluoroalkyl group is preferred).

$A^{11}$ to $A^{15}$ are preferably an aromatic hydrocarbon ring group which may have a substituent and more preferably a phenylene group that bonds at the first site and the fourth site.

In General Formula (2), the divalent linking group represented by $Z^{11}$ to $Z^{14}$ is not particularly limited, and, for example, the same divalent linking group as the divalent linking group described in the above-described paragraph of $Z^1$ to $Z^4$ are exemplified. As $Z^{11}$ to $Z^{14}$, particularly, —COO—, —OCO—, or —CH=CH— is preferred.

In General Formula (2), $m^3$ and $m^4$ each independently represent an integer of 0 or 1 and are preferably 0.

The compound represented by General Formula (2) can be synthesized using a well-known method.

Hereinafter, specific examples of the compound represented by General Formula (2) will be shown, but are not limited thereto.

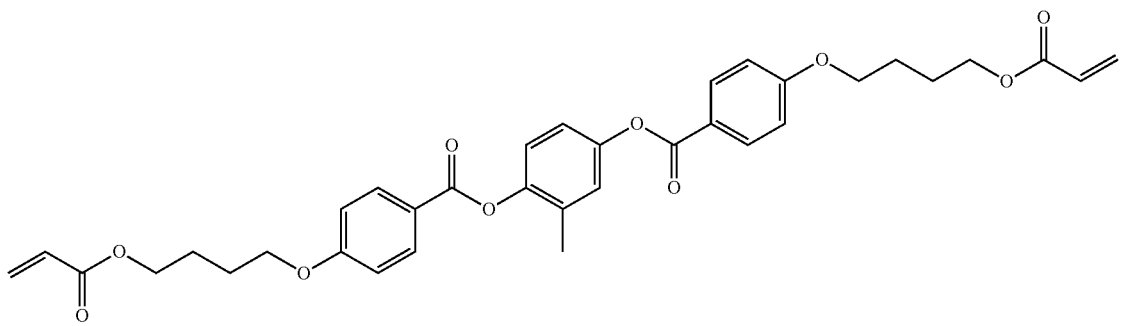

LC-1

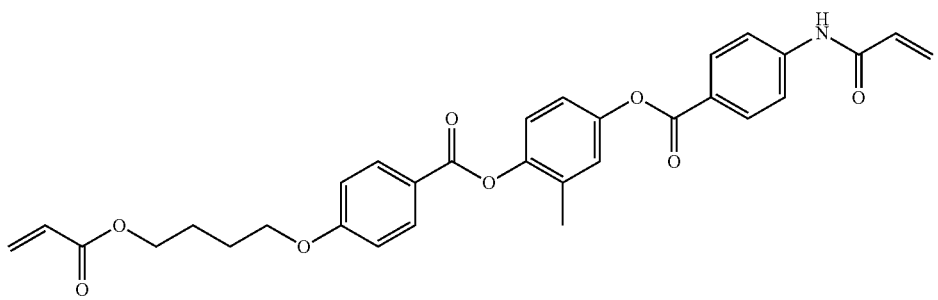

LC-2

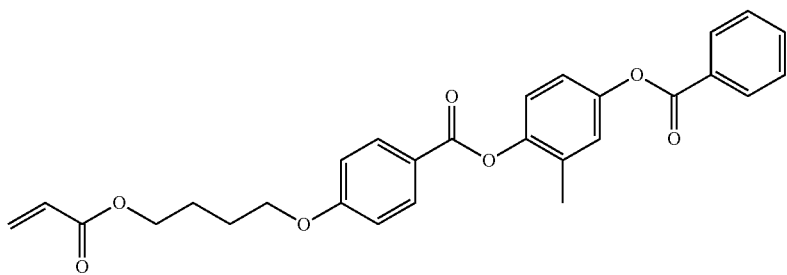

LC-3

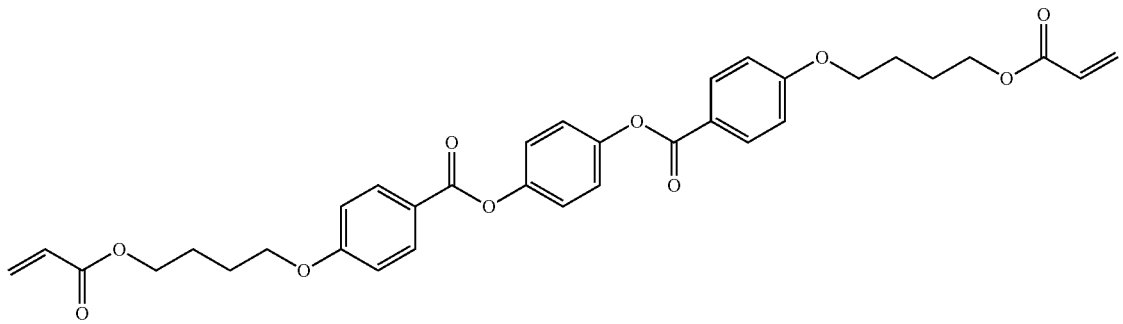

LC-4

-continued
LC-5
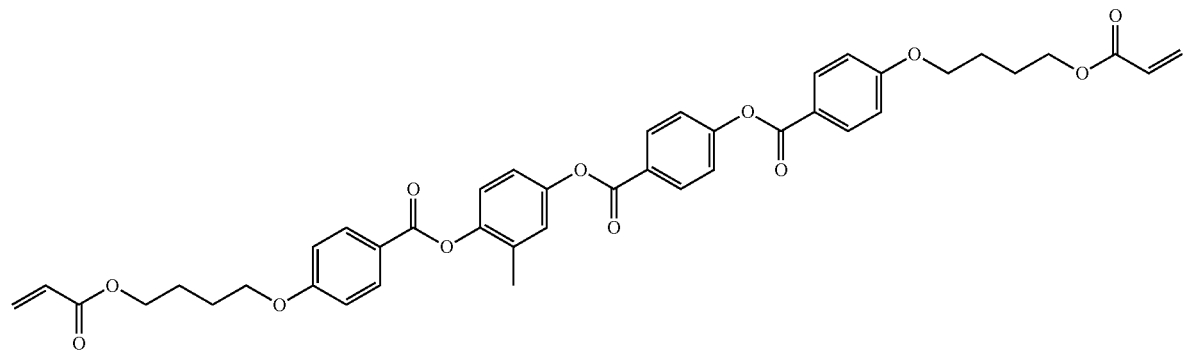
LC-6
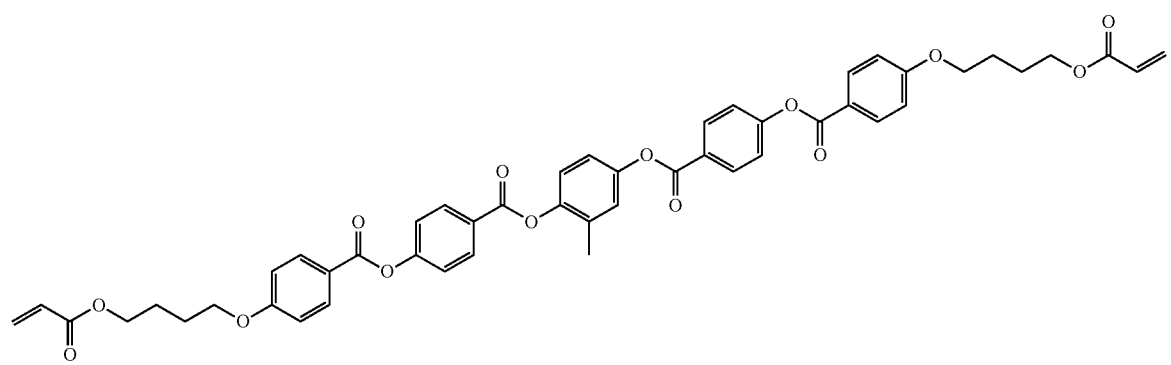
LC-7
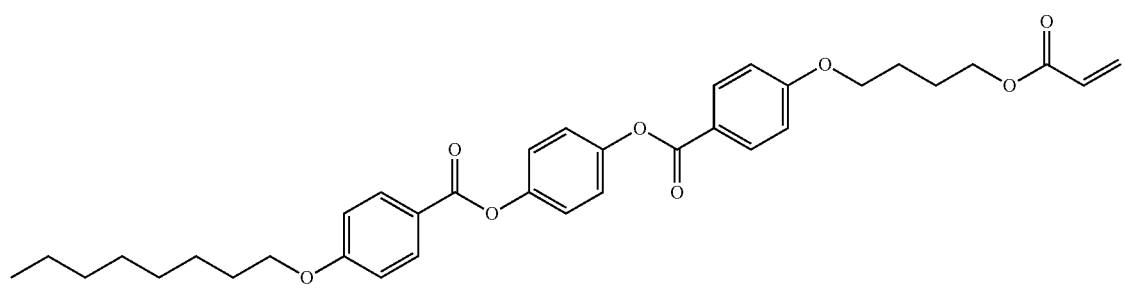
LC-8
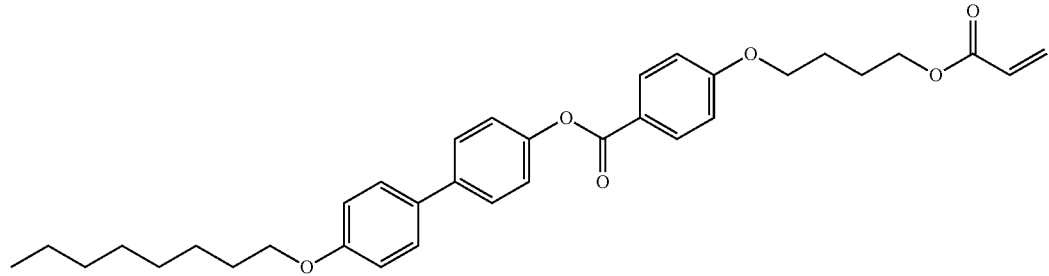

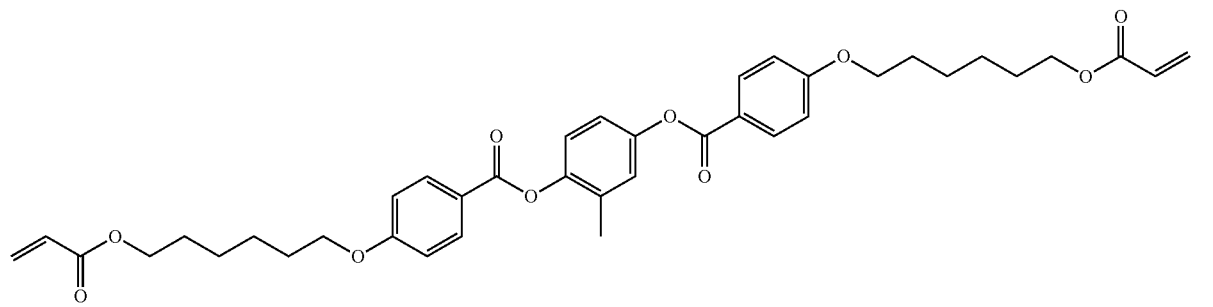

LC-9

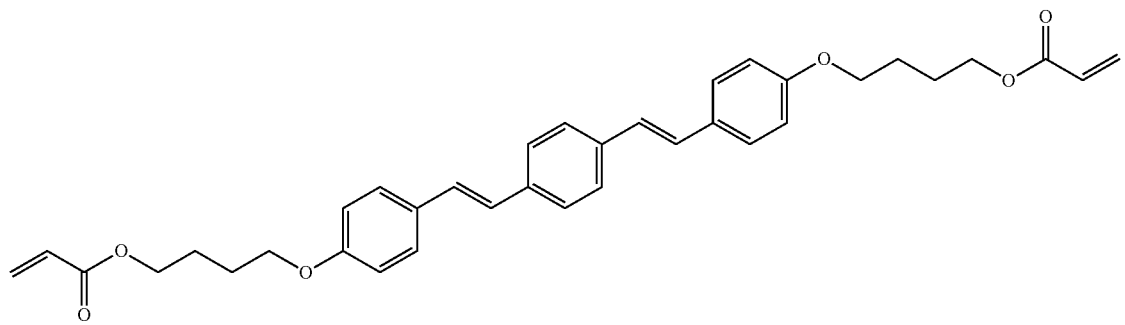

LC-10

The compound represented by General Formula (2) may be used singly or a plurality of the compounds may be used in combination.

The content of the liquid crystalline compound in the liquid crystal composition of the embodiment of the present invention is preferably 5% to 99% by mass, more preferably 25% to 98% by mass, and still more preferably 75% to 98% by mass of the total mass of the liquid crystal composition.

<Compound Represented by General Formula (1)>

The liquid crystal composition of the embodiment of the present invention contains the compound represented by General Formula (1). The compound represented by General Formula (1) is as described above.

The compound represented by General Formula (1) may be used singly or a plurality of the compounds may be used in combination.

The content of the compound represented by General Formula (1) in the liquid crystal composition of the embodiment of the present invention is preferably 1% to 20% by mass, more preferably 2% to 15% by mass, and still more preferably 2% to 10% by mass of the total mass of the liquid crystalline compound.

(Polymerization Initiator)

The liquid crystal composition may include a polymerization initiator.

The polymerization initiator is preferably a photopolymerization initiator capable of initiating a polymerization reaction by irradiation with ultraviolet rays. As the photopolymerization initiator, for example, an α-carbonyl Compound, an acyloin ether, an α-hydrocarbon-substituted aromatic acyloin compound, a polynuclear quinone compound, a phenazine compound, and an oxadiazole compound are exemplified.

The content of the polymerization initiator in the liquid crystal composition is not particularly limited, but is preferably 0.1% to 20% by mass and more preferably 1% to 8% by mass of the total mass of the liquid crystalline compound.

In addition to the above-described components, the liquid crystal composition may include other additives such as a solvent, a surfactant, an antioxidant, an ultraviolet absorber, a sensitizer, a stabilizer, a plasticizer, a chain transfer agent, a polymerization inhibitor, a antifoaming agent, a leveling agent, a thickener, a flame retardant, a dispersant, a polymerizable monomer, and a color material such as a dye or a pigment.

The liquid crystal composition can be applied to a variety of applications. For example, an optical anisotropic body or a reflection film can be formed using the liquid crystal composition. For example, in a case where the liquid crystalline compound has a polymerizable group, a cured substance is obtained by carrying out a curing treatment (light irradiation treatment, a heating treatment, or the like) on the liquid crystal composition, and the cured substance can be preferably applied to an optical anisotropic body or a reflection film.

The optical anisotropic body refers to a substance having optical anisotropy.

In addition, the reflection film corresponds to a layer obtained by fixing a cholesteric liquid crystal phase and is capable of reflecting light in a predetermined reflection band.

The compound represented by General Formula (1) has a high temperature dependence of HTP. Therefore, in the case of carrying out a step 1 and a step 2 described below on the compound, a reflection layer in which a bright portion and a dark portion have a wavy structure in a cross-sectional scanning electron microscopic (SEM) observation view is formed.

Step 1: A step of applying the liquid crystal composition onto a substrate and heating the applied liquid crystal composition, thereby orienting the liquid crystalline compound and producing a cholesteric liquid crystal phase state Step 2: A step of cooling the liquid crystal composition so that the temperature of the composition decreases to be higher than or equal to a predetermined value (for example, 30° C. or higher), thereby forming a reflection layer A reflection layer as described above is excellent not only in terms of transparency but also in terms of diffusion reflectivity and thus can be preferably applied to a transparent screen and the like. A curing treatment may be carried out during the step 2 or after the step 2 as necessary.

EXAMPLES

Hereinafter, the present invention will be described in more detail on the basis of examples. Materials, Materials, amounts used, proportions, processing contents, processing orders, and the like described in the following examples can be appropriately modified within the scope of the gist of the present invention. Therefore, the scope of the present invention is not supposed to be interpreted in a limited manner by specific examples described below.

Example 1

<Synthesis of Compound CD-1>
A compound CD-1 was synthesized according to the following scheme.

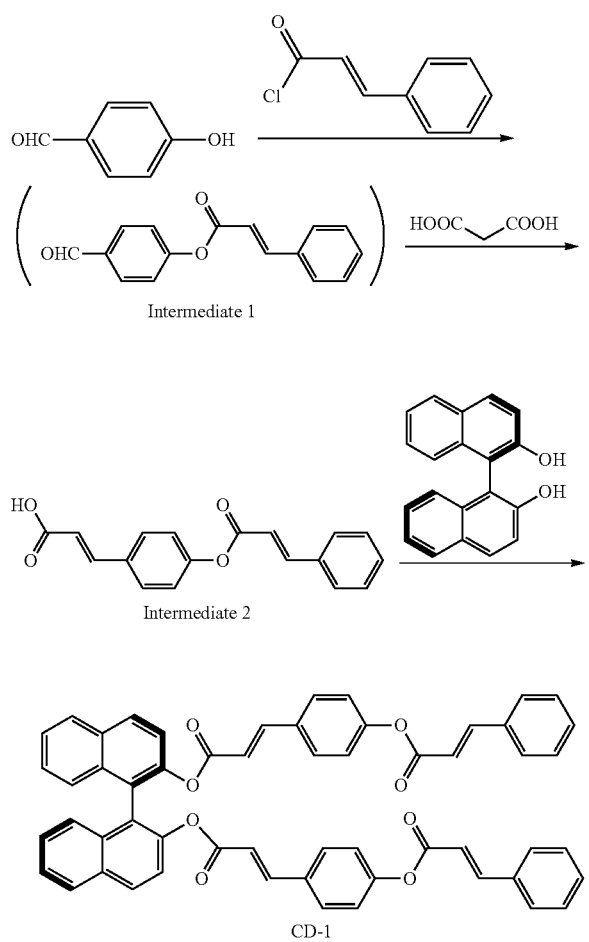

(Synthesis of Immediate 2)

Para-hydroxybenzaldehyde (manufactured by Wako Pure Chemical Industries, Ltd.) (53.31 g), N-methyl-2-pyrrolidone (NMP, manufactured by Wako Pure Chemical Industries, Ltd.) (153 mL), and potassium carbonate (manufactured by Wako Pure Chemical Industries, Ltd.) (72.40 g) were put into a 2 L three-neck flask, then, cinnamoyl chloride (manufactured by Tokyo Chemical Industry Co., Ltd.) (80.00 g) was further added to the three-neck flask, and a reaction liquid was reacted at 40° C. for two hours. Subsequently, ethyl acetate (manufactured by Wako Pure Chemical Industries, Ltd.) (500 mL) and water (300 mL) were added to the reaction liquid, the obtained reaction liquid was stirred at 40° C. for 15 minutes, and then, a water phase was removed, thereby obtaining an ethyl acetate solution of an intermediate 1.

Subsequently, malonic acid (manufactured by Wako Pure Chemical Industries, Ltd.) (68.1 g) and pyridine (manufactured by Wako Pure Chemical Industries, Ltd.) (17.6 mL) were added to the ethyl acetate solution of the intermediate 1 and were reacted for three hours while ethyl acetate was distilled away under a nitrogen flow at 100° C. Next, methanol (manufactured by Wako Pure Chemical Industries, Ltd.) (60 mL) and water (400 mL) were added to the obtained product, and a generated solid was filtered and dried by blowing air at 40° C. for 12 hours, thereby obtaining an intermediate 2 (123 g, yield: 96%).

(Synthesis of Compound CD-1)

The intermediate 2 (100 g), acetonitrile (manufactured by Wako Pure Chemical Industries, Ltd.) (600 mL), and dimethylacetamide (manufactured by Wako Pure Chemical Industries, Ltd.) (400 mL) were put into a 2 L three-neck flask, then, thionyl chloride (manufactured by Wako Pure Chemical Industries, Ltd.) (42.23 g) was further added to the three-neck flask, and a reaction liquid was reacted at 60° C. for one hour. Subsequently, the reaction liquid was cooled to 5° C., (R)-binaphthol (manufactured by Kanto kagaku) (47.7 g), and pyridine (manufactured by Wako Pure Chemical Industries, Ltd.) (134.1 g) were added to the reaction liquid, and the reaction liquid was reacted at 40° C. for five hours. Next, methanol (manufactured by Wako Pure Chemical Industries, Ltd.) (600 mL) and water (1,000 mL) were added to the reaction liquid, and a generated solid was filtered and dried by blowing air at 40° C. for 12 hours, thereby obtaining a compound CD-1 (100 g, yield: 72%).

The result of $^1$HNMR (heavy solvent: Dimethylsulfoxide (DMSO)-$d_6$) of the compound CD-1 is shown in FIG. 1.

<Evaluation of Helical Twisting Power (HTP) and Temperature Dependence Thereof>

HTP and the temperature dependence thereof were evaluated using the compound CD-1 that corresponds to the compound represented by General Formula (1).

(Preparation of Specimen Solution)

A liquid crystalline compound LC-1 represented by the following structure and the compound CD-1 were mixed together, and then a solvent is added to the obtained mixture, thereby preparing a specimen solution having the following composition.

Liquid crystalline compound LC-1 represented by the following structure: 100 parts by mass Compound CD-1: 5 parts by mass Solvent (methyl ethyl ketone (MEK))/cyclohexanone=90/10 (mass ratio)): An amount at which the solute concentration reached 30% by mass

LC-1

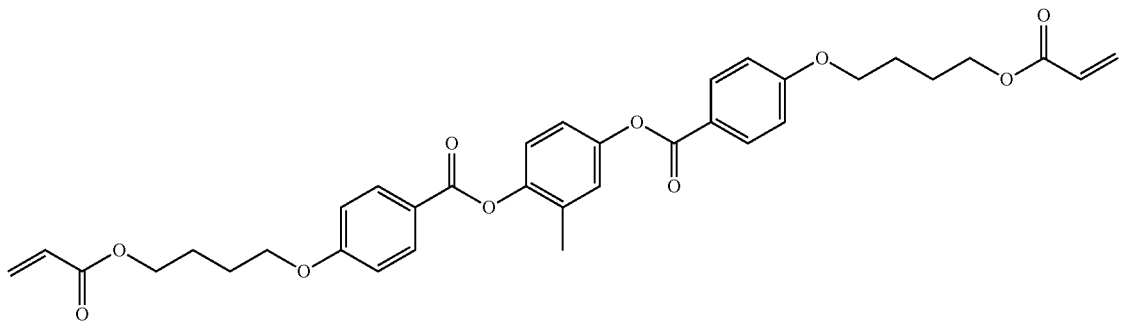

(Production of Liquid Crystal Layer 1)

Next, a polyimide orientation film SE-130 (manufactured by Nissan Chemical Corporation) was applied onto a washed glass substrate, thereby forming a coated film. The obtained coated film was fired and then rubbed, thereby producing an orientation film-attached substrate. The rubbed surface of the orientation film was spin-coated with the specimen solution (30 μL) under conditions of a rotation rate of 1,000 rpm and 10 seconds, thereby forming a liquid crystal layer.

For the obtained liquid crystal layer, the helical twisting power (HTP) and the temperature dependence were computed.

(Computation of HTP)

HTP's at 40° C. and 90° C. were computed from Equation (1) below.

HTP=(average refractive index of liquid crystalline compound)/{(concentration (% by mass) of chiral compound with respect to liquid crystalline compound)×(central reflection wavelength (nm) at each temperature)}[μm$^{-1}$]  Equation (1):

In Equation (1), "average refractive index of liquid crystalline compound" was assumed to be 1.55 in the computation. In addition, for "central reflection wavelength at each temperature", the central reflection wavelength was measured using a microscope (manufactured by Nikon Corporation, ECLIPSE E600-POL) and a spectral photometer (manufactured by Ocean Optics, USB-4000/USB4H09800) in a state in which the produced liquid crystal layer was heated to 40° C. and 90° C. respectively using a hot stage (manufactured by Mettler Toledo, FP90/FP82HT).

(Computation of Temperature Dependence of HTP)

The temperature dependence of HTP was computed from Equation (2) below, thereby evaluating the temperature dependence of HTP.

Temperature change rate={(HTP at 40° C.)−(HTP at 90° C.)}/(HTP at 40° C.)×100 [%]  Equation (2):

HTP and the temperature dependence thereof were evaluated using the values computed from Equation (1) and Equation (2) on the basis of the following evaluation standards. The results are shown in Table 1.

<<Evaluation Standards>>

"A": HTP at 40° C. is 30 μm$^{-1}$ or more, and the temperature change rate is 13% or more.

"B+": HTP at 40° C. is 30 μm$^{-1}$ or more, and the temperature change rate is 11% or more and less than 13%.

"B": HTP at 40° C. is 30 μm$^{-1}$ or more, and the temperature change rate is 9% or more and less than 11%.

"C": HTP at 40° C. is 30 μm$^{-1}$ or more, and the temperature change rate is 7% or more and less than 9%.

"D": HTP at 40° C. is less than 30 μm$^{-1}$, and the temperature change rate is 7% or more.

"E": The temperature change rate is less than 7%.

Examples 2 to 21

Compounds CD-2 to CD-21 were synthesized according to the synthesis method of the compound CD-1 and evaluated in the same manner as in Example 1 as Examples 2 to 21. The results are shown in Table 1.

Hereinafter, the compounds CD-2 to CD-21 will be shown.

CD-2

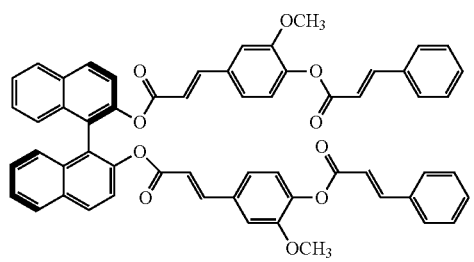

CD-3

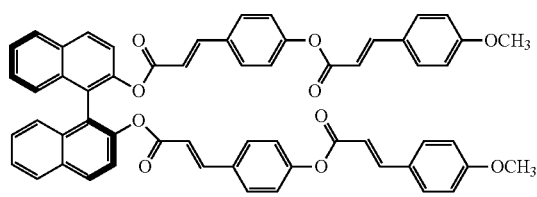

-continued
CD-4
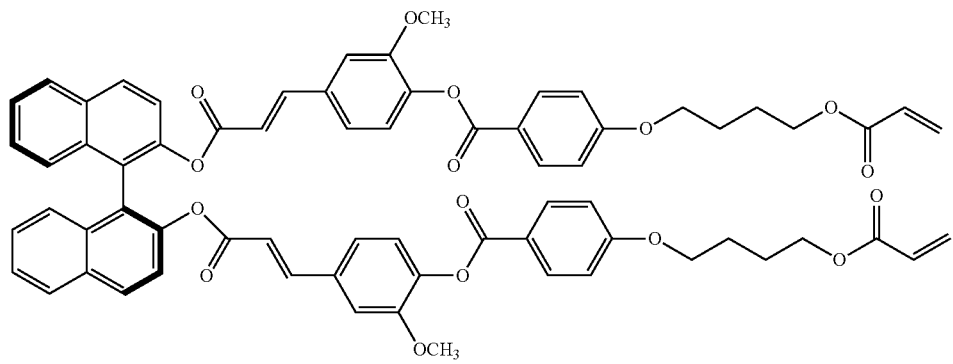
CD-5
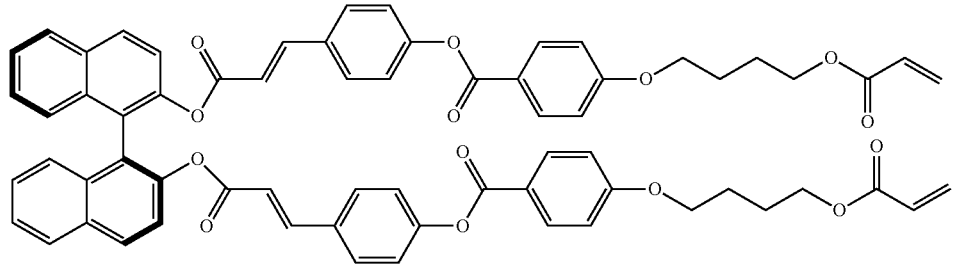
CD-6 CD-7
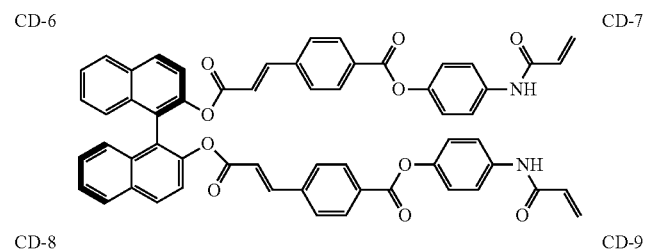
CD-8 CD-9
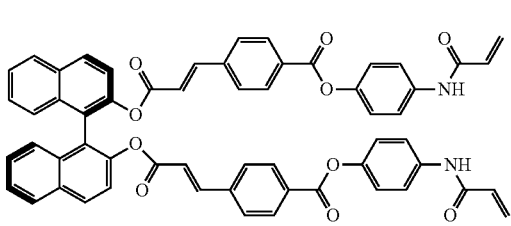
CD-10 CD-11
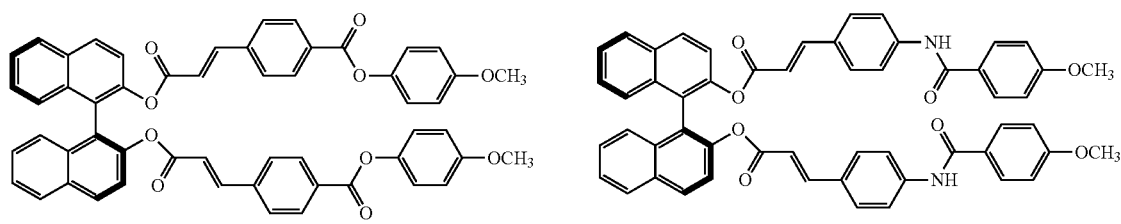
CD-12 CD-13
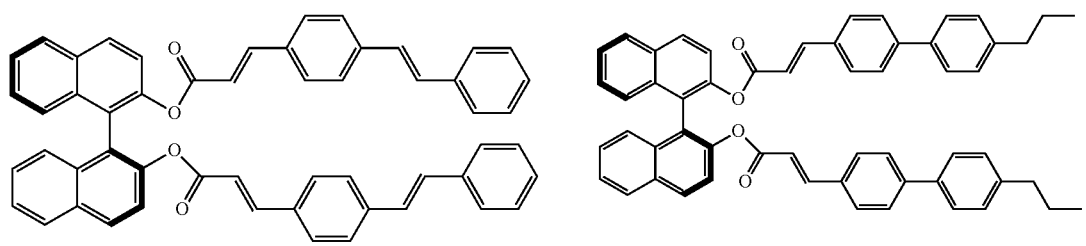
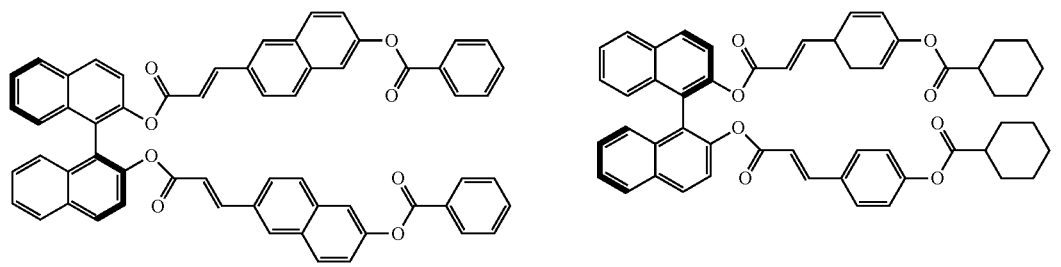

CD-14
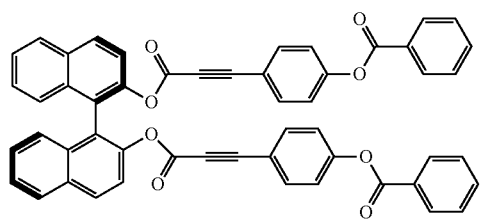
CD-15
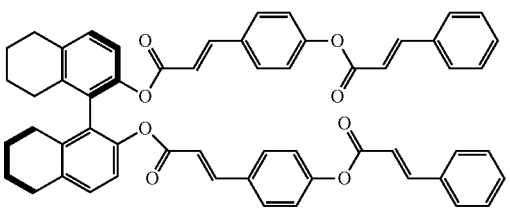
CD-16
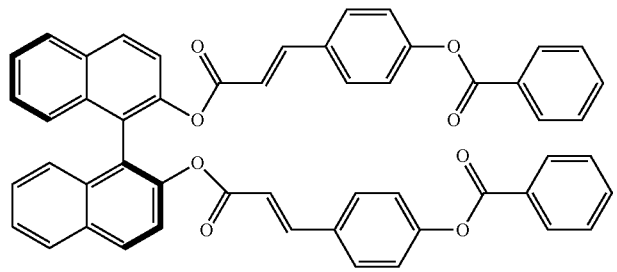
CD-17
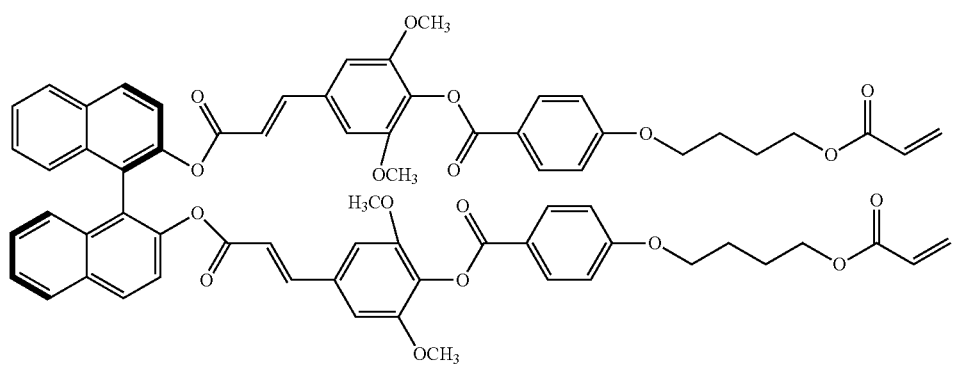
CD-18
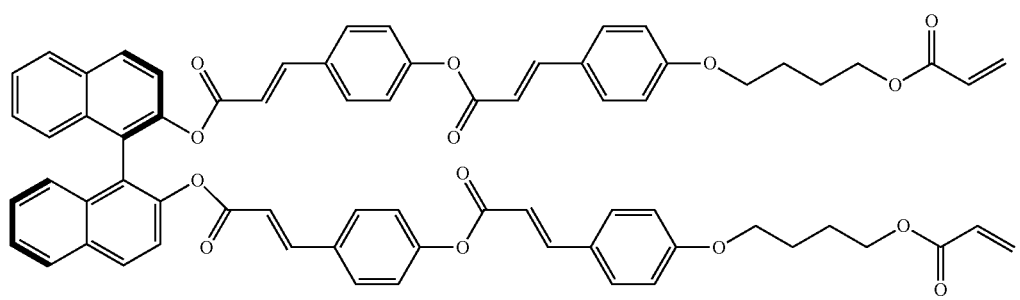
CD-19
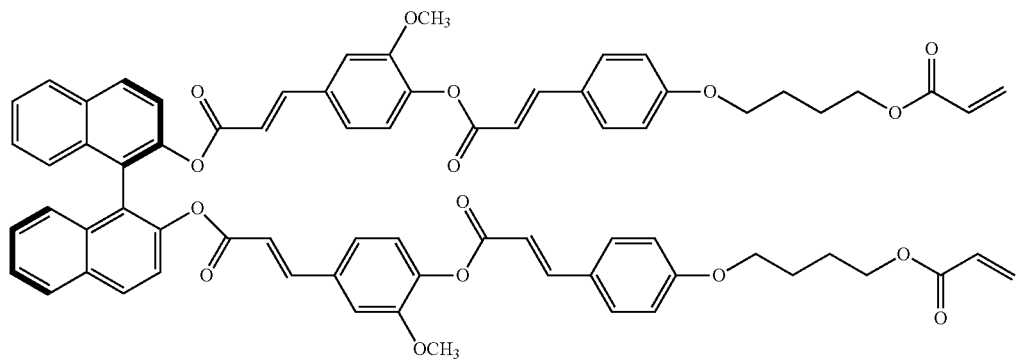

CD-20

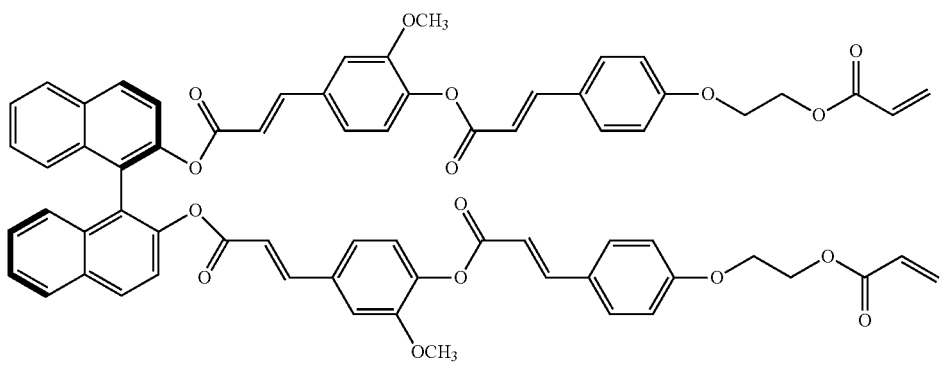

CD-21

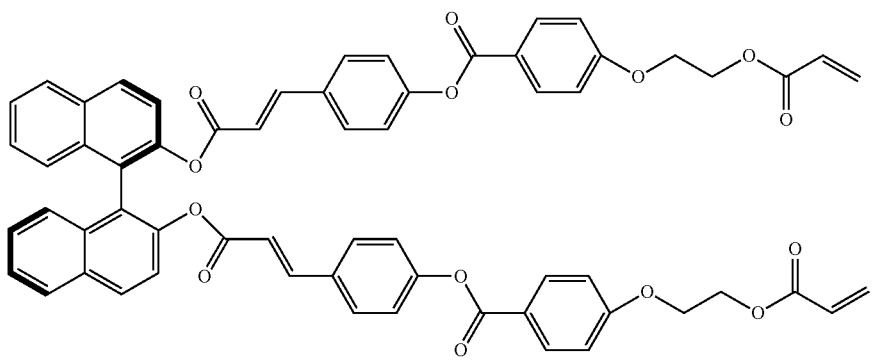

Comparative Examples 1 to 8

Comparative compounds CCD-1 to CCD-4 were prepared on the basis of an ordinary synthesis method. Regarding the synthesis method, p. 35 to 70 of "The Fifth Series of Experimental Chemistry 16" edited by The Chemical society of Japan was referred to. In addition, Nf19 and Nf20 exemplified on page 12 of JP2007-176927A and I21 and I23 exemplified on page 10 of JP2013-087109A were prepared respectively as CCD-5 to CCD-8. These compounds were evaluated in the same manner as in Example 1 as Comparative Examples 1 to 8. The results are shown in Table 1.

Hereinafter, the comparative compounds CCD-1 to CCD-8 will be shown.

CCD-2

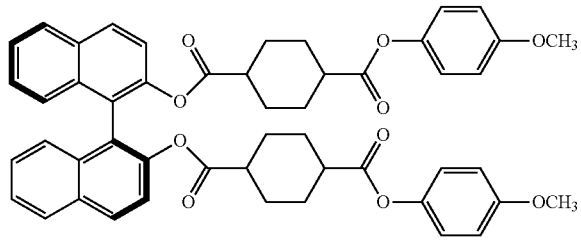

CCD-3

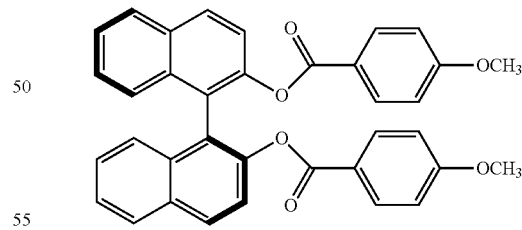

CCD-1

CCD-4

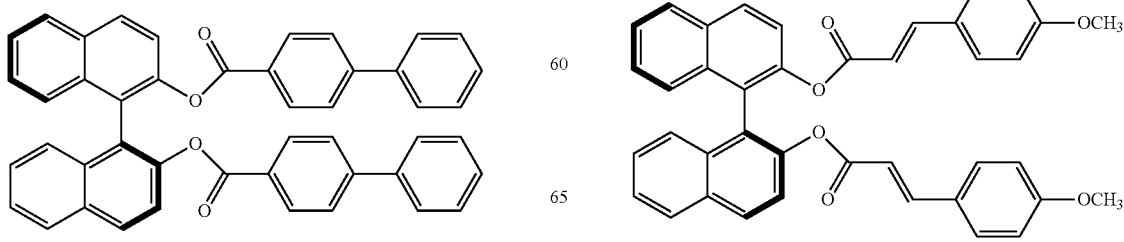

-continued

CCD-5

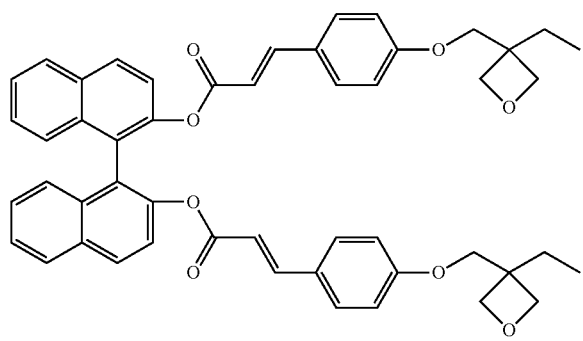

The comparative compound CCD-5 corresponds to Nf19 exemplified on page 12 of JP2007-176927A.

CCD-6

The comparative compound CCD-6 corresponds to Nf20 exemplified on page 12 of JP2007-176927A.

CCD-7

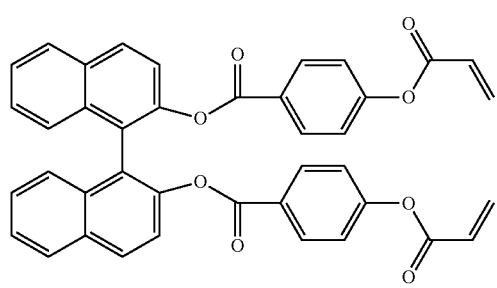

The comparative compound CCD-7 corresponds to I21 exemplified on page 10 of JP2013-087109A.

CCD-8

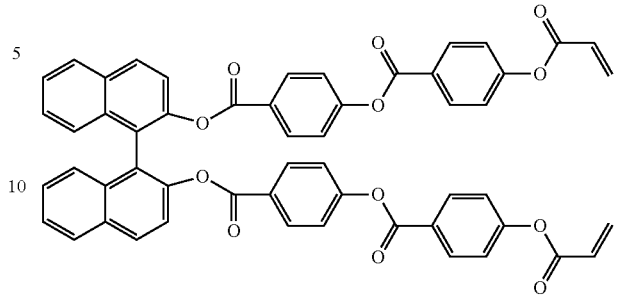

The comparative compound CCD-8 corresponds to I23 exemplified on page 10 of JP2013-087109A.

TABLE 1

| | Kind of chiral compound | Evaluation of HTP and temperature dependence |
|---|---|---|
| Example 1 | CD-1 | A |
| Example 2 | CD-2 | A |
| Example 3 | CD-3 | B |
| Example 4 | CD-4 | B |
| Example 5 | CD-5 | B |
| Example 6 | CD-6 | B |
| Example 7 | CD-7 | B |
| Example 8 | CD-8 | B |
| Example 9 | CD-9 | C |
| Example 10 | CD-10 | C |
| Example 11 | CD-11 | C |
| Example 12 | CD-12 | C |
| Example 13 | CD-13 | C |
| Example 14 | CD-14 | C |
| Example 15 | CD-15 | B |
| Example 16 | CD-16 | B |
| Example 17 | CD-17 | B |
| Example 18 | CD-18 | B+ |
| Example 19 | CD-19 | B+ |
| Example 20 | CD-20 | A |
| Example 21 | CD-21 | B |
| Comparative Example 1 | CCD-1 | E |
| Comparative Example 2 | CCD-2 | E |
| Comparative Example 3 | CCD-3 | D |
| Comparative Example 4 | CCD-4 | D |
| Comparative Example 5 | CCD-5 | D |
| Comparative Example 6 | CCD-6 | D |
| Comparative Example 7 | CCD-7 | D |
| Comparative Example 8 | CCD-8 | E |

The above-describe results show that all of the compounds of the examples had a strong HTP and a high temperature dependence.

In addition, the comparison between Examples 1 to 11 and Examples 16 to 21 shows that, in a case where $Z^1$ and $Z^2$ in General Formula (1) of the present invention are —COO—, —OCO—, —CH=CH—COO—, —CH=CH—OCO—, —COO—CH=CH—, or —OCO—CH=CH— (preferably —CH=CH—COO—, —CH=CH—OCO—, —COO—CH=CH—, or —OCO—CH=CH—), the temperature dependence of HTP is higher.

In addition, the comparison between Example 3 and Example 12 shows that, in a case where $A^1$ and $A^2$ in General Formula (1) of the present invention are a phenylene group which may be substituted, the temperature dependence of HTP is higher.

In addition, the comparison between Example 3 and Example 13 shows that, in a case where $A^3$ and $A^4$ in General Formula (1) of the present invention are a five- or more-membered aromatic hydrocarbon ring group which may be substituted, the temperature dependence of HTP is higher.

In addition, the comparison between Example 3 and Example 14 shows that, in a case where $X^1$ and $X^2$ in General Formula (1) of the present invention are —CH=CH—, the temperature dependence of HTP is higher.

In addition, the comparison between Example 1 and Example 15 shows that, compared with the compound represented by General Formula (1A-3) of the present invention, the compound represented by General Formula (1A-4) has a higher temperature dependence of HTP.

In the case of comparing Example 4, Example 5, and Example 17, it was confirmed that, these examples were all evaluated as "B" in Table 1, but Example 4 and Example 17 had a higher temperature dependence of HTP than Example 5. In addition, the same tendency is confirmed in the comparison between Example 1 and Example 2 and the comparison between Example 18 and Example 19. In other words, it is confirmed that Example 1 and Example 18 have a higher temperature dependence of HTP than Example 2 and Example 19 respectively. From these results, it is clear that, in a case where $A^1$ and $A^2$ in General Formula (1) of the present invention has a substituent (particularly, has an alkoxy group having 1 to 6 carbon atoms as the substituent), the temperature dependence of HTP is higher.

In addition, from the results of Example 19 and Example 20, it was also confirmed that, in a case where the monovalent substituent represented by $R^1$ and $R^2$ in General Formula (1) of the present invention represents the group (*-$L^4$-P) represented by General Formula (PA) and the divalent linking group represented by $L^A$ represents a —O-alkylene group (here, the alkylene group is a linear or branched alkylene group having 1 to 3 carbon atoms), the temperature dependence of HTP is higher. The same tendency is confirmed in the comparison between Example 5 and Example 21 (Example 5 and Example 21 were all evaluated as "B" in Table 1, but the temperature dependence of HTP of Example 21 is higher than that of Example 5).

On the other hand, it was shown that the compounds of the comparative examples failed to satisfy the desired requirements. From the results of the comparative examples, it was confirmed that, in a case where the group that directly bonds to the *$^a$ and *$^b$ sites (2, 2' sites) of the binaphthyl skeleton is not the group corresponding to the —OCO—X'-$A^1$- group (or the —OCO—$X^2$-$A^2$- group) in General Formula (1) of the present invention, there is a tendency that the temperature dependence of HTP is low (Comparative Examples 1, 2 and 8).

In the compounds of Comparative Examples 3 and 7, the group that directly bonded to the *$^a$ and *$^b$ sites (2, 2' sites) of the binaphthyl skeleton was not the group corresponding to the —OCO—$X^1$-$A^1$- group (or the —OCO—$X^2$-$A^2$- group) in General Formula (1) of the present invention, but there was one five- or more-membered hydrocarbon ring group or heterocyclic group in each of the substituents in the *$^a$ and *$^b$ sites (2, 2' sites) of the binaphthyl skeleton, and thus the flexibility of the binaphtyl skeleton was considered to improve more than in Comparative Examples 1, 2, and 8; however, as the results, the temperature dependence of HTP was more favorable than those in Comparative Examples 1, 2, and 8, but the HTP values failed to reach the desired level.

In addition, in the compounds of Comparative Examples 4 to 6, there was one five- or more-membered hydrocarbon ring group or heterocyclic group in each of the substituents in the *$^a$ and *$^b$ sites (2, 2' sites) of the binaphthyl skeleton, and thus the HTP values failed to reach the desired level.

Example 22

<Production and Evaluation of Reflection Film>

A reflection film was produced from a liquid crystal composition in which the compound CD-1 (Example 1) corresponding to the compound represented by General Formula (1) and evaluated.

(Preparation of Specimen Solution)

The liquid crystalline compound LC-1, the compound CD-1, a surfactant (1) represented by the following structure, and a polymerization initiator were mixed together, and then a solvent is added to the obtained mixture, thereby preparing a specimen solution having the following composition.

Liquid crystalline compound LC-1: 100 mg
Compound CD-1: 5 mg
Surfactant (1): 0.1 mg
Polymerization initiator (Irg-819 (manufactured by BASF)): 3 mg
Solvent (methyl ethyl ketone (MEK))/cyclohexanone=90/10 (mass ratio)): An amount at which the solute concentration reached 30% by mass

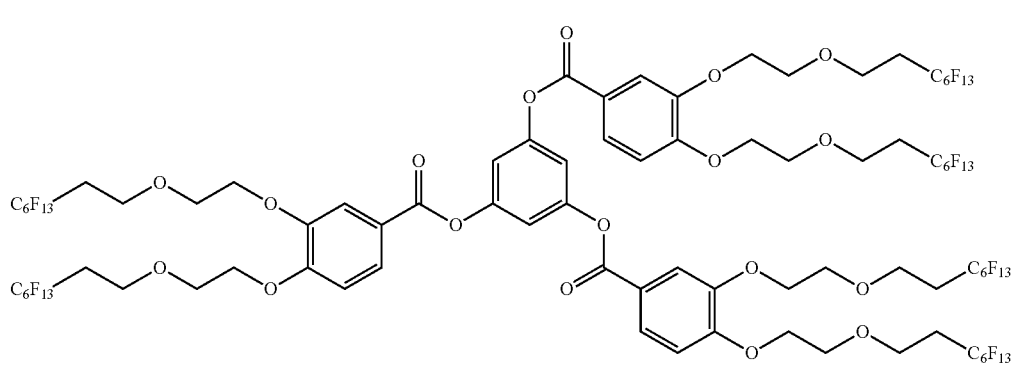

Surfactant (1)

(Production of Reflection Film)

Next, a polyimide orientation film SE-130 (manufactured by Nissan Chemical Corporation) was applied onto a washed glass substrate, thereby forming a coated film. The obtained coated film was fired and then rubbed, thereby producing an orientation film-attached substrate. The rubbed surface of the orientation film was spin-coated with the specimen solution (30 µL) under conditions of a rotation rate of 1,000 rpm and 10 seconds to form a coated film, and the coated film was dried at 90° C. for one minute. After drying, the coated film was irradiated with ultraviolet rays (UV) in an irradiation amount of 500 mJ/m² at 25° C. to cure the coated film, thereby obtaining a reflection film.

In the case of observing a surface of the obtained reflection film using an optical microscope, a grid pattern was observed due to the transformation of the phase of the cholesteric liquid crystal phase. Furthermore, the obtained reflection film exhibited an excellent broad-angle reflection characteristic.

What is claimed is:

1. A compound represented by General Formula (1) below,

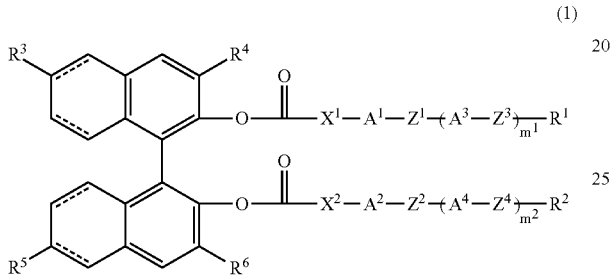

(1)

in General Formula (1), $X^1$ and $X^2$ each independently represent —CH=CH— or C≡C—, $A^1$ to $A^4$ each independently represent a five- or more-membered hydrocarbon ring group or a five- or more-membered heterocyclic group which may have a substituent selected from the group consisting of a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group, $Z^1$ to $Z^4$ each independently represent a single bond or a divalent linking group, $m^1$ and $m^2$ each independently represent an integer of 1 to 5, $R^1$ and $R^2$ each independently represent a hydrogen atom, or a monovalent substituent selected from the group consisting of a halogen atom, an alkyl group, an alkenyl group, an alkenyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, an alkoxycarbonyl group, and a group represented by General Formula (PA) being *-$L^A$-P, wherein $L^A$ represents a single bond or a divalent linking group, P represents a group represented by one of General Formulae (P-1) to (P-11) and (P-14) to (P-20), and * represents a bonding position,

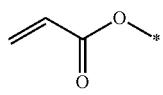

(P-1)

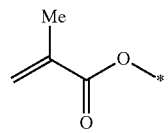

(P-2)

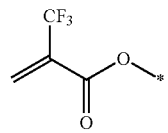

(P-3)

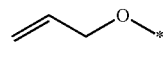

(P-4)

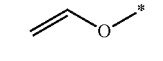

(P-5)

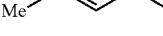

(P-6)

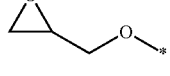

(P-7)

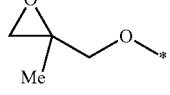

(P-8)

(P-9)

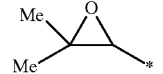

(P-10)

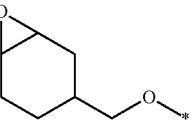

(P-11)

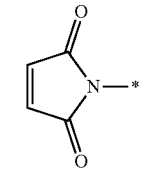

(P-14)

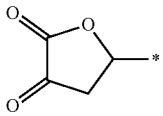

(P-15)

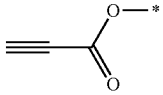

(P-16)

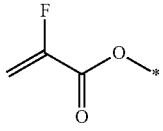

(P-17)

-continued

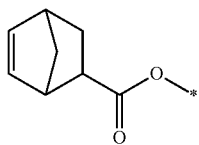
(P-18)

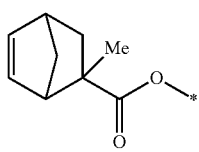
(P-19)

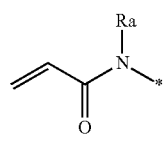
(P-20)

R³ to R⁶ each independently represent a hydrogen atom, or a monovalent substituent selected from the group consisting of a halogen atom, an alkyl group, an alkenyl group, an alkynyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, an alkoxycarbonyl group, and a group represented by General Formula (PA') being *-$L^{A'}$-P', wherein $L^{A'}$ represents a single bond or a divalent linking group, P' represents a group represented by one of the above General Formulae (P-1) to (P-11) and (P-14) to (P-20) and General Formulae (P-12) and (P-13), and * represents a bonding position, and

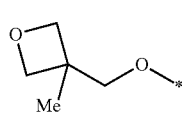
(P-12)

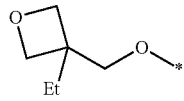
(P-13)

the portion in which a solid line and a broken line are parallel to each other represents a single bond or a double bond.

2. The compound according to claim 1, wherein the $A^1$ and the $A^2$ each are independently a five- or more-membered aromatic hydrocarbon ring group which may have a substituent selected from the group consisting of a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group.

3. The compound according to claim 1, wherein the $A^1$ and the $A^2$ each are independently a phenylene group which may have a substituent selected from the group consisting of a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group.

4. The compound according to claim 1, wherein the $X^1$ and the $X^2$ are —CH=CH—.

5. The compound according to claim 1, wherein the $A^3$ and the $A^4$ each are independently a five- or more-membered aromatic hydrocarbon ring group which may have a substituent selected from the group consisting of a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group.

6. The compound according to claim 1, wherein the $Z^1$ and the $Z^2$ each are independently —COO—, —OCO—, —CH=CH—COO—, —CH=CH—OCO—, —COO—CH=CH—, or —OCO—CH=CH—.

7. The compound according to claim 1, wherein the $Z^1$ and the $Z^2$ each are independently —CH=CH-13 COO—, —CH=CH—OCO—, —COO—CH=CH—, or —OCO—CH=CH—.

8. The compound according to claim 1, wherein the $Z^3$ and the $Z^4$ each are independently a single bond, —CH=CH—COO—, —CH=CHO—CO—, —COO—CH=C—, or —OCO—CH=CH—.

9. A liquid crystal composition comprising:
a liquid crystalline compound; and
the compound according to claim 1.

10. The liquid crystal composition according to claim 9, wherein the liquid crystalline compound is a liquid crystalline compound having at least one polymerizable group.

11. The liquid crystal composition according to claim 10, wherein the liquid crystalline compound is a compound represented by General Formula (2) below,

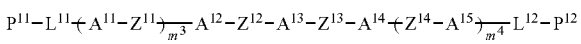

(2)

in General Formula (2),
$P^{11}$ and $P^{12}$ each independently represent a hydrogen atom or a polymerizable group; here, at least one of $P^{11}$ or $P^{12}$ represents a polymerizable group,
$L^{11}$ and $L^{12}$ each independently represent a single bond or a divalent linking group,
$A^{11}$ to $A^{15}$ each independently represent an aromatic hydrocarbon ring group or an aromatic heterocyclic group which may have a substituent selected from the group consisting of a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitrile group, and an alkoxycarbonyl group,
$Z^{11}$ to $Z^{14}$ each independently represent a single bond or a divalent linking group, and
$m^3$ and $m^4$ each independently represent an integer of 0 or 1.

12. A cured substance formed by carrying out a curing treatment on the liquid crystal composition according to claim 9.

13. An optical anisotropic body comprising the cured substance according to claim 12.

14. A reflection film comprising the cured substance according to claim 12.

15. The compound according to claim 1,
wherein the $Z^1$ and the $Z^2$ each independently represent a divalent linking group.

16. The compound according to claim 1,
wherein the $Z^3$ and the $Z^4$ are each independently —COO—CH=CH—, or —OCO—CH=CH—.

17. The liquid crystal composition according to claim 11,
wherein the aromatic hydrocarbon ring group or the aromatic heterocyclic group as the $A^{13}$ has a monocyclic structure.

18. The liquid crystal composition according to claim 17,
wherein when any one of the $m^3$ and the $m^4$ represents an integer of 1, $Z^{12}$ or $Z^{13}$ represents a divalent linking group.

* * * * *